(12) United States Patent
Sawadkar et al.

(10) Patent No.: US 11,738,112 B2
(45) Date of Patent: Aug. 29, 2023

(54) TISSUE SCAFFOLD

(71) Applicant: Raft Enterprises Limited, Northwood Middlesex (GB)

(72) Inventors: Prasad Sawadkar, Northwood Middlesex (GB); Elena Garcia-Gareta, Northwood Middlesex (GB)

(73) Assignee: Raft Enterprises Limited, Northwood Middlesex (GB)

(*) Notice: Subject to any disclaimer, the term of this patent is extended or adjusted under 35 U.S.C. 154(b) by 711 days.

(21) Appl. No.: 16/630,638

(22) PCT Filed: Jul. 13, 2018

(86) PCT No.: PCT/GB2018/052002
§ 371 (c)(1),
(2) Date: Jan. 13, 2020

(87) PCT Pub. No.: WO2019/012295
PCT Pub. Date: Jan. 17, 2019

(65) Prior Publication Data
US 2020/0164104 A1    May 28, 2020

(30) Foreign Application Priority Data
Jul. 14, 2017    (GB) .................................. 1711360

(51) Int. Cl.
*A61L 27/22* (2006.01)
*A61L 27/24* (2006.01)
*A61L 27/52* (2006.01)
*C12N 5/00* (2006.01)

(52) U.S. Cl.
CPC ........... *A61L 27/227* (2013.01); *A61L 27/225* (2013.01); *A61L 27/24* (2013.01); *A61L 27/52* (2013.01); *C12N 5/0062* (2013.01); *A61L 2430/40* (2013.01); *C12N 2513/00* (2013.01); *C12N 2533/54* (2013.01); *C12N 2533/56* (2013.01); *C12N 2537/10* (2013.01)

(58) Field of Classification Search
CPC ...... A61L 27/227; A61L 27/225; A61L 27/24; A61L 27/52; A61L 2430/40; A61L 27/3683; C12N 5/0062; C12N 2513/00; C12N 2533/54; C12N 2533/56; C12N 2537/10
See application file for complete search history.

(56) References Cited

U.S. PATENT DOCUMENTS

| | | | |
|---|---|---|---|
| 6,881,226 B2 | 4/2005 | Corbitt, Jr. | |
| 9,433,489 B2 | 9/2016 | Reilly et al. | |
| 10,722,336 B2 | 7/2020 | Mathisen et al. | |
| 2004/0136977 A1 | 7/2004 | Miyamoto | |
| 2007/0104692 A1 | 5/2007 | Quijano et al. | |
| 2008/0096812 A1 | 4/2008 | Okamoto et al. | |
| 2008/0107708 A1 | 5/2008 | Ng et al. | |
| 2010/0249927 A1 | 9/2010 | Yang et al. | |
| 2011/0229574 A1 | 9/2011 | Guillen et al. | |
| 2014/0005784 A1 | 1/2014 | Van Epps et al. | |
| 2016/0143726 A1 | 5/2016 | Kemnitzer et al. | |
| 2021/0353831 A1 | 11/2021 | Seidner et al. | |

FOREIGN PATENT DOCUMENTS

| | | |
|---|---|---|
| DE | 10 2006 029 605 A1 | 12/2007 |
| EP | 1 403 304 A1 | 3/2004 |
| EP | 2 068 766 B1 | 6/2009 |
| JP | 2008-291258 A | 12/2008 |
| JP | 2010-148922 A | 7/2010 |
| JP | WO2010/110067 A1 | 9/2010 |
| JP | 2014-183886 A | 10/2014 |
| WO | WO 99/45941 A1 | 9/1999 |
| WO | 2004/087232 A1 | 10/2004 |
| WO | 2008/037028 A1 | 4/2008 |
| WO | 2021/191897 A1 | 9/2021 |

OTHER PUBLICATIONS

Definition of fractionate by Dictionary.com retrieved form Dictionary.com on Oct. 21, 2022, 1 page of PDF.*
European Communication dated Dec. 23, 2021 received in European Application No. 18 745 693.4.
Adair G.S. et al., "A Soluble Protein Derived from Elastin", 167(4250):605 (Apr. 14, 1951).
Annabi N. et al., "Synthesis of Highly Porous Crosslinked Elastin Hydrogels and Their Interaction with Fibroblasts In Vitro", Biomaterials 30:4550-4557 (2009).
Auerbach R. et al., "A Simple Procedure for the Long-Term Cultivation of Chicken Embryos", Developmental Biology 41:391-394 (1974).
Banga I et al., "Structure and Function of Elastin and Collagen", Book Reviews, pp. 220-221 (1966).
Buttafoco L. et al., "Electrospinning of Collagen and Elastin for Tissue Engineering Applications", Biomaterials 27:724-734 (2006).
Daamen W.F. et al., "Elastin as a Biomaterial for Tissue Engineering", Biomaterials 28:4378-4398 (Nov. 2007).
Fu W. et al., "Electrospun Gelatin/PCL and Collagen/PLCL Scaffolds for Vascular Tissue Engineering", International Journal of Nanomedicine 9:2335-2344 (2014).
Ghasemi-Mobarakeh L. et al., "Structural Properties of Scaffolds: Crucial Parameters Towards Stem Cells Differentiation", Worid Journal of Stem Cells 7(4):728-744 (May 26, 2015).
Gray W.R. et al., "Molecular Model for Elastin Structure and Function", Nature 246:461-466 (Dec. 21/28, 1973).
Huang W. et al., "Silk-Elastin-Like Protein Biomaterials for the Controlled Delivery of Therapeutics", Expert Opin Drug Deliv. 12(5):779-791 (May 2015).

(Continued)

*Primary Examiner* — Kade Ariani
(74) *Attorney, Agent, or Firm* — Scully, Scott, Murphy & Presser, P.C.

(57) ABSTRACT

There is provided a tissue scaffold and a method for making a tissue scaffold. The tissue scaffold comprises elastin and optionally fibrin and/or collagen. The elastin in the scaffold may be cross-linked. The elastin that is cross-linked preferably comprises solubilised elastin and is unfractionated.

18 Claims, 27 Drawing Sheets
Specification includes a Sequence Listing.

(56) References Cited

OTHER PUBLICATIONS

Lake S.P. et al., "Mechanics of a Fiber Network Within a Non-Fibrillar Matrix: Model and Comparison With Collagen-Agarose Co-Gels", Ann Biomed Eng 40(10):2111-2121 (Oct. 2012).
Leach J.B. et al., "Crosslinked α-Elastin Biomaterials: Towards a Processable Elastin Mimetic Scaffold", Acta Biomaterialia 1:155-164 (2005).
Majd H. et al., "Dynamic Expansion Culture for Mesenchymal Stem Cells", Methods in Molecular Biology 698:175-188 (2011).
Nivison-Smith L. et al., "Elastin Based Constructs", Regenerative Medicine and Tissue Engineering-Cells and Biomaterials, Chapter 15, Elastin Based Constructs ISBN978-953-307-663-8 DOI: 10.5772/837 (2011).
Ryan A.J. et al., "Insoluble Elastin Reduces Collagen Scaffold Stiffness, Improves Viscoelastic Properties, and Induces a Contractile Phenotype in Smooth Muscle Cells", Biomaterials 73:296-307 (2015).
Skopinska-Wisniewska J. et al., "Collagen/Elastin Hydrogels Cross-Linked by Squaric Acid", Materials Science and Engineering C 60:100-108 (2016).
Stoklasová A. et al., "Soluble Elastins, Their Preparation and Characterization", Sb Ved Pr Lek Fak Karlovy Univerzity Hradci Kralove 35(3):217-223 (1992), English-language abstract only.
Zhang D. et al., "The Effect of Mesenchymal Stem Cell Shape on the Maintenance of Multipotency", Biomaterials 34:3962-3969 (2013).
International Search Report and Written Opinion dated Oct. 12, 2018 issued in PCT/GB2018/052002.
GB Search Report dated Jan. 15, 2018 issued in GB 1711360.6.
Wise, Steven et al., "Engineered tropoelastin and elastin-based biomaterials", Advances in Protein Chemistry and Structural Biology (Jan. 1, 2009), vol. 78, No. 1, pp. 1-24.
Miyamoto, Keiichi et al., "Creation of cross-linked electrospun isotypic elastin fibers controlled cell-differentiation with new cross-linker", International Journal of Biological Macromolecules (2009), vol. 45, No. 1, pp. 33-41.

* cited by examiner

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
cgcctgagca aagtaaatga g                                        21

<210> SEQ ID NO 2
<211> LENGTH: 19
<212> TYPE: DNA
<213> ORGANISM: Artificial Sequence
<220> FEATURE:
<223> OTHER INFORMATION: Synthetic primer

<400> SEQUENCE: 2
gccctcgata tagcggatg                                           19

<210> SEQ ID NO 3
<211> LENGTH: 25
<212> TYPE: DNA
<213> ORGANISM: Artificial Sequence
<220> FEATURE:
<223> OTHER INFORMATION: Synthetic primer

<400> SEQUENCE: 3
gaataaagat ggggttctca tatcc                                    25

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
aacttcagca aactcaaact t                                        21

<210> SEQ ID NO 5
<211> LENGTH: 25
<212> TYPE: DNA
<213> ORGANISM: Artificial Sequence
<220> FEATURE:
<223> OTHER INFORMATION: Synthetic primer

<400> SEQUENCE: 5
cggcaactct agtatttagg ataac                                    25

<210> SEQ ID NO 6
<211> LENGTH: 24
<212> TYPE: DNA
<213> ORGANISM: Artificial Sequence
<220> FEATURE:
<223> OTHER INFORMATION: Synthetic primer

<400> SEQUENCE: 6
caaataaaat gacaaggcac gatt                                     24

<210> SEQ ID NO 7
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 7 ttctccccttt ttcccactga                                              20

<210> SEQ ID NO 8
<211> LENGTH: 25
<212> TYPE: DNA
<213> ORGANISM: Artificial Sequence
<220> FEATURE:
<223> OTHER INFORMATION: Synthetic primer

<400> SEQUENCE: 8
caaacgcaat cactatctat accat                                         25

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9
ggaccagtac ccgcacttg                                                19

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
aatccgggtg gtccttcttg                                               20

<210> SEQ ID NO 11
<211> LENGTH: 23
<212> TYPE: DNA
<213> ORGANISM: Artificial Sequence
<220> FEATURE:
<223> OTHER INFORMATION: Synthetic primer

<400> SEQUENCE: 11
cactaaggaa ggaattggga aca                                           23

<210> SEQ ID NO 12
<211> LENGTH: 25
<212> TYPE: DNA
<213> ORGANISM: Artificial Sequence
<220> FEATURE:
<223> OTHER INFORMATION: Synthetic primer

<400> SEQUENCE: 12
gggattaaaa tcaagagcat cattg                                         25

<210> SEQ ID NO 13
<211> LENGTH: 18
<212> TYPE: DNA
<213> ORGANISM: Artificial Sequence
<220> FEATURE:
<223> OTHER INFORMATION: Synthetic primer

<400> SEQUENCE: 13
cgtttcgtgt ccctttca                                                 18
```

```
<210> SEQ ID NO 14
<211> LENGTH: 25
<212> TYPE: DNA
<213> ORGANISM: Artificial Sequence
<220> FEATURE:
<223> OTHER INFORMATION: Synthetic primer

<400> SEQUENCE: 14
cctcttgttc attcttgttc gtatt                                              25
```

TISSUE SCAFFOLD

This invention concerns tissue scaffolds, such as elastin-based tissue scaffolds and methods for forming such scaffolds.

INCORPORATION BY REFERENCE OF SEQUENCE LISTING

The Sequence Listing in an ASCII text file, named as 38113_Sequence_Listing.txt of 3 KB, created on Jan. 2, 2020, and submitted to the United States Patent and Trademark Office via EFS-Web, is incorporated herein by reference.

Elastin is an extracellular structural protein found in connective tissues such as skin, adipose, lung, tendon, ligament, arteries, or cartilage. Its primary function is to retain the shape of tissues after stretching or contraction and has load bearing properties (Banga, 1966; Gray, 1973). In vivo, elastin forms by the process of elastogenesis, through the assembly and cross-linking of the protein tropoelastin (encoded by the ELN gene).

Tropoelastin typically consists of hydrophobic domains with many Gly, Val, Ala and Pro residues which often occur in repeats of several amino acids, such as Gly-Val-Gly-Val-Pro, Gly-Val-Pro-Gly-Val and Gly-Val-Gly-Val-Ala-Pro; and hydrophobic domains with many Lys and Ala residues which are important in cross-linking. Cross-linking of tropoelastin to form elastin is facilitated by lysyl oxidase.

Elastin is one of the most stable and abiding proteins in humans with a half-life of 74 years. Its excellent structural and biological properties has attracted attention for tissue engineering applications (Daamen et al., 2007). For example, elastin provides elasticity to tissues and organs, and is abundant where elasticity is of primary importance, such as blood vessels, ligaments, in lung and in skin. However, elastin is a highly insoluble protein therefore, it remains a challenge to use it as a biomaterial (Leach et al., 2005).

To overcome this challenge many existing strategies have been developed for $\alpha$-elastin, a form of soluble elastin obtained following hydrolysis with oxalic acid. However, this process is expensive, time consuming and the total yield is minimal. Consequently, its clinical translation to a scaffold is questionable.

Some studies have reported mixing insoluble elastin with other materials, such as collagen (Ryan and O'Brien, 2015). However, the resulting scaffolds have weaker mechanical properties and altered biological responses compared to collagen itself.

The inventors report novel and economical, biologically active elastin-based materials and methods for their fabrication.

This invention concerns the formation of a scaffold by cross-linking a composition comprising elastin, such as solubilised elastin.

The invention also concerns a tissue scaffold comprising cross-linked elastin.

According to the invention, there is provided a method for forming a tissue scaffold comprising cross-linking a composition comprising solubilised elastin.

According to the invention, there is provided a method comprising cross-linking a composition, wherein the composition comprises elastin that has been contacted by a solubilising agent that can solubilise the elastin.

According to the invention, there is provided a method comprising: a) contacting elastin with a solubilising agent that is able to solubilise the elastin; and b) cross-linking the elastin composition formed in step a).

According to the invention, there is provided a tissue scaffold comprising cross-linked, solubilised elastin.

The elastin may be extracted or derived from a natural source. For example, the elastin may be derived from a mammalian source. The mammalian source may be a bovine source, such as bovine neck ligament, or a human source. Alternatively, the elastin may be recombinant elastin.

Elastin is a highly insoluble protein due to inter-chain cross-links. However, it can be solubilised (Daamen (2007)). Solubilised elastin is also referred to as hydrolysed elastin or elastin peptides.

Common methods of solubilising elastin include treating it with 0.25 M oxalic acid at 100° C., or treating it with 1M KOH in 80% ethanol. In addition, proteolytic enzymes capable of degrading elastic fibres, including serine-type elastases from polymorphonuclear leukocytes and several metallo-elastases of monocyte/macrophage origin, also result in solubilised elastin. Examples of hydrolysed forms of elastin are show in the table below.

| Type | Preparation Method | Molecular mass |
| --- | --- | --- |
| $\alpha$ | Oxalic acid solubilisation | Heterogeneous mixture, average 60 kDa |
| $\beta$ | Oxalic acid solubilisation | Heterogeneous mixture, average 3-10 kDa |
| $\kappa$ | KOH solubilisation | Heterogeneous mixture, average 70 kDa |
| PSP | Pepsin solubilisation | Heterogeneous mixture, average 25 KDa |
| ASP | Acid solubilisation | Heterogeneous mixture, average 25 kDa. |
| ESP | Elastase solubilisation | Heterogeneous mixture |

Elastin peptides obtained after oxalic acid hydrolysis can be coacervated after suspension in 10 mM sodium acetate with 10 mM NaCl set to pH 5.5 with acetic acid, followed by heating and centrifugation at 37° C. As a result of this, two fractions are formed, $\alpha$-elastin (a viscous coacervate) and $\beta$-elastin (in the supernatant).

The prior art has focussed mainly on using insoluble elastin in combination with other components, such as collagen, or has focussed on the $\alpha$-elastin soluble component obtained following hydrolysis with oxalic acid and separation from $\beta$-elastin. Surprisingly, however, the inventors have found that solubilising elastin, and cross-linking the product of that solubilisation step, can form a promising and cost-effective tissue scaffold. So, there is no requirement to separate or isolate fractions of elastin, such as separating or isolating $\alpha$-elastin and $\beta$-elastin. The solubilised elastin that is cross-linked may thus be considered crude or unfractionated. Advantageously, the invention may avoid the time, inconvenience and expense associated with isolating the $\alpha$-elastin fraction. The invention may also improve total yield, as a step to separate $\alpha$-elastin and $\beta$-elastin can be avoided.

According to the invention, there is provided a method for forming a tissue scaffold comprising cross-linking a composition comprising unfractionated solubilised elastin.

According to the invention, there is provided a method comprising cross-linking a composition comprising elastin, wherein the elastin is unfractionated and the elastin comprises solubilised, elastin. The method may involve contacting elastin with a solubilising agent that is able to solubilise at least some of the elastin and then cross-linking the resulting composition.

The unfractionated elastin may thus be crude elastin in which there has been no purification, isolation, separation or refinement of one or more elastin fractions, or one or more different forms of elastin which result from the contact of elastin with a solubilising agent. For instance, there may not have been isolation of one or more soluble elastin fractions, or separation of an insoluble elastin fraction from a soluble elastin fraction. Consequently, the composition may comprise different soluble forms of elastin. The composition may comprise elastin that has not been solubilised. The composition may thus comprise both soluble and insoluble forms of elastin. For example, following contact with the solubilising agent, the elastin may not be subjected to centrifugation. There may be no fractionation, purification, isolation, separation or refinement of the elastin following contact with the solubilising agent.

Surprisingly, the inventors have appreciated that an effective elastin-based tissue scaffold can be formed without requiring fractionation of elastin, in which one or more fractions of elastin are isolated and the isolated fraction(s) are subsequently used to form a scaffold. For example, the invention may not require isolation and utilisation of an α-elastin fraction. Advantageously, the present invention may not require conventional steps to fractionate the elastin, such as centrifugation and/or coacervation. Also advantageously, compositions comprising both soluble and insoluble elastin may be used. This may provide a significant benefit over known methods. For example, US2004/0136977 requires isolation of water-soluble elastin, involving centrifugation. JP2014183886 requires sequential rounds of acid fractionation of insoluble elastin, involving centrifugation.

The invention does not encompass methods comprising cross-linking of tropoelastin by, for example, the cross-linking of tropoelastin by lysyl oxidase, or the products of such methods.

Methods of the invention may comprise the step of solubilising the elastin. This may involve contacting the elastin with a solubilising agent that is able to solubilise at least some of the elastin. So, the invention may provide a method comprising: a) solubilising elastin to form a composition comprising unfractionated, solubilised elastin; b) cross-linking the product obtained from step a).

According to the invention, there is provided a method comprising: a) solubilising elastin to form a composition comprising solubilised elastin; b) cross-linking the composition obtained from step a).

According to the invention, there is provided a method comprising: a) contacting elastin with a solubilising agent to form a composition comprising solubilised elastin; and b) cross-linking the composition obtained from step a).

According to the invention, there is provided a method comprising cross-linking elastin that has been contacted with a solubilising agent, wherein the elastin has not been fractionated.

According to the invention, there is provided a method comprising cross-linking a composition, the composition comprising elastin, wherein the elastin is unfractionated and comprises solubilised elastin.

According to the invention, there is provided a tissue scaffold comprising cross-linked unfractionated solubilised elastin.

According to the invention, there is provided a tissue scaffold comprising cross-linked elastin, wherein the composition comprising cross-liked elastin has been formed by cross-linking a formulation comprising elastin that comprises solubilised elastin and wherein the elastin has not been fractionated.

According to the invention, there is provided a tissue scaffold comprising cross-linked elastin, wherein the elastin has been contacted with a solubilising agent and has not been fractionated.

The scaffold may be prepared from a solution comprising 1 to 20% (w/v) elastin, for example 5 to 15% (w/v) elastin, such as around 10% (w/v) elastin.

Preferably, the elastin is, or has been, solubilised by contacting with acid, most preferably oxalic acid.

According to the invention, there is provided a method of solubilising elastin comprising contacting elastin with a solubilising agent that is able to solubilise at least some of the elastin. The solubilising agent is preferably an acid, more preferably oxalic acid.

According to the invention, there is provided a method of solubilising elastin comprising contacting elastin with an acid, preferably oxalic acid.

In a particularly preferred embodiment, the elastin is solubilised at a temperature less than 100° C., preferably at a temperature of less than or equal to 50° C., more preferably at a temperature of 15 to 30° C., such as room temperature.

The acid, preferably oxalic acid, may be at less than 1M, preferably less than 0.75M, more preferably at 0.5M, or less than 0.5M. The acid may be at least 0.25M. For example, the acid may be at 0.2M to 1M, for example 0.25M to 0.75M.

The method of solubilising elastin, as described herein, is contrary to the established method of solubilising elastin using oxalic acid. The conventional method of solubilising elastin using oxalic acid is carried out at 100° C. (see, for example, Daamen et al. (2007)). However, the inventors have found that effective solubilisation, for the purposes of forming a scaffold of the invention, may occur at temperatures less than 100° C. Although not wishing to be bound by theory, the inventors have postulated that the treatment with oxalic acid at temperatures less than 100° C. may lead to formation of a mixture comprising α- and β-elastin. If this is the case, methods of the invention may comprise cross-linking α- and β-elastin, and scaffolds of the invention may comprise cross-linked α- and β-elastin. Advantageously, the inventors have appreciated that it is not necessary to separate solubilised fractions, such as isolating the α-elastin fraction, and that a crude, or unfractionated, mixture of solubilised elastin can be used to form an effective scaffold. It is appreciated that compositions comprising solubilised elastin, such as unfractionated solubilised elastin, may comprise some elastin that has not been solubilised. The composition may thus comprise a mixture of insoluble elastin and soluble elastin.

The invention may thus provide a method comprising cross-linking a composition comprising soluble elastin and insoluble elastin. The invention may thus provide a tissue scaffold comprising cross-linked elastin, wherein the elastin comprises soluble elastin and insoluble elastin.

Surprisingly, the inventors have appreciated that complete solubilisation of the elastin to be cross-linked, may not be required to obtain an effective tissue scaffold.

According to the invention, there is provided a method comprising cross-linking a composition comprising insoluble elastin.

According to the invention, there is provided a tissue scaffold comprising cross-linked, insoluble elastin.

Solubilisation, or contact with acid, preferably takes place for at least 30 seconds, more preferably at least one minute. For example, the solubilisation or contact with acid may take place for about 1 to 3 minutes. The solubilisation, or contact with acid, may take place for up to 5 minutes. This contrasts with the conventional treatment of elastin with oxalic acid which typically takes place for about 1 hour (see, for instance, US2004/0136777).

According to the invention there is provided a method comprising contacting elastin with acid, preferably oxalic acid. Preferably, contact with the acid takes place at a temperature less than 100° C., most preferably at a temperature of less than or equal to 50° C., more preferably at a temperature of 15 to 30° C., such as room temperature or ambient temperature. The method may further comprise cross-linking the resulting product.

According to the invention, there may be provided a method of forming a tissue scaffold comprising cross-linking a composition comprising α-elastin and β-elastin.

According to the invention, there may be provided a tissue scaffold comprising a cross-linked composition comprising α-elastin and β-elastin.

Cross-linking may occur using any one of a number of cross-linking agents or cross-linking techniques commonly known to those skilled in the art, such as chemical, radiation and dehydrothermal methods.

References herein to "cross-linking" concern covalent cross-linking. Preferably, cross-linking is achieved non-enzymatically, using a chemical cross-linking agent.

Cross-linking may occur in the presence of the solubilising agent (e.g. acid such as oxalic acid). So, the invention may provide, or make use of, a composition comprising elastin, a solubilising agent and a cross-linking agent.

Examples of suitable chemical cross-linking agents include: carbodiimide coupling agents such as N-(3-dimethylaminopropyl)-N-ethylcarbodiimide (EDC); N-hydroxysuccinimide (NHS), azide coupling agents; diisocyanate cross-linking agents such as hexamethylene diisocyanate; epoxide cross-linking agents such as epi-chlorhydrin, glycidylethers and glycidylamines; and aldehyde cross-linking agents such as formaldehyde, glutaraldehyde and glyoxal.

The chemical cross linking agent may comprises N-(3-dimethylaminopropyl)-N'-ethylcarbodiimide (EDC) and/or N-hydroxysuccinimide (NHS).

The chemical cross linking agent may comprise aldehyde cross-linking agents such as formaldehyde, glutaraldehyde and glyoxal. Aldehyde cross-linking agents may have the advantage of providing extracellular matrix compositions with improved biocompatibility. In a preferred embodiment, the aldehyde cross-linking agent is glutaraldehyde. The use of glutaraldehyde as a cross-linking agent may provide an advantage of yielding an optimal cross-link density more rapidly than other aldehydes and is also capable of achieving a relatively high density of cross-linking. In a preferred example, the chemical cross-linking agent is glutaraldehyde.

During the cross-linking step, the cross-linking agent may be present in an amount of about 0.2 to 5% (v/v), such as 0.5 to 3% (v/v), preferably 0.5 to 1.5% (v/v), e.g. 1% (v/v).

When the cross-linking agent comprises glutaraldehyde or N-(3-dimethylaminopropyl)-N'-ethylcarbodiimide (EDC) and/or N-hydroxysuccinimide (NHS), the method according to the invention may additionally comprise the addition of a toxicity reducing agent (e.g. lysine or sodium borohydride).

The step of cross-linking the composition comprising solubilised elastin may be carried out at a temperature of 20° C. to 50° C., preferably about 37° C. Contact or incubation with the cross-linking agent may typically be performed between 1 minute and 24 hours (e.g. 4 hours). For example the cross-linking may take place for about an hour, or at least one hour. The cross-linking may take place in the presence of $CO_2$, for example at least 2% $CO_2$ (by volume), for example 2 to 10% $CO_2$ (by volume), or at about 5% $CO_2$ (by volume).

According to the invention, there is provided a composition comprising elastin, a solubilising agent for solubilising elastin, and a cross-linking agent.

Methods of the invention may comprise casting the composition comprising solubilised elastin. Casting may comprise applying the composition comprising solubilised elastin to a mould of a predetermined shape. The casting may occur prior to or during cross-linking. It is preferred that methods of the invention comprise lyophilisation following cross-linking. For example, the composition may be frozen at −80° C., preferably overnight, and then lyophilised for about 48 hours. Preferably, lyophilisation occurs for at least 24 hours.

According to the invention, there is provided a method comprising lyophilising a composition comprising cross-linked elastin. According to the invention, there is provided a method comprising lyophilising a composition comprising solubilised and cross-linked elastin. For example, there is provided a method comprising lyophilising a composition, the composition comprising cross-linked unfractionated solubilised elastin.

According to the invention, there is provided a method of forming a tissue scaffold comprising lyophilising a composition comprising cross-linked elastin, wherein the composition comprising cross-liked elastin has been formed by cross-linking a formulation comprising elastin that is unfractionated and that comprises solubilised elastin.

According to the invention, there is provided a method comprising:
a) solubilising elastin; b) cross-linking solubilised elastin obtained from step a); and c) lyophilising the product from step b).

According to the invention, there is provided a method comprising:
a) solubilising elastin; b) cross-linking unfractionated solubilised elastin obtained from step a); and c) lyophilising the product from step b).

According to the invention, there is provided a method comprising: a) contacting elastin with a solubilising agent that is able to solubilise the elastin to form a composition comprising solubilised elastin; b) cross-linking the composition produced in step a); and c) lyophilising the product of step b).

According to the invention, there is provided a tissue scaffold comprising lyophilised, cross-linked elastin.

According to the invention, there is provided a tissue scaffold comprising lyophilised, cross-linked, solubilised elastin.

According to the invention, there is provided a tissue scaffold comprising lyophilised, cross-linked unfractionated solubilised elastin.

According to the invention, there may be provided a method comprising lyophilising a composition comprising cross-linked α-elastin and β-elastin.

According to the invention, there may be provided a tissue scaffold comprising lyophilised, cross-linked α-elastin and β-elastin.

According to the invention there may be provided a tissue scaffold comprising lyophilised, cross-linked elastin, wherein the cross-linked elastin has been formed by cross-linking a composition comprising soluble elastin and insoluble elastin.

Methods of the invention may comprise washing or cleaning to remove agents involved in solubilising and/or cross-linking. Washing preferably takes place following solubilisation. This may include contacting or washing with a reducing agent, particularly if the cross-linking agent comprises an aldehyde cross-linking agent. Washing may comprise ultrasonic cleaning. For example, the scaffold may be washed using water in an ultrasonic cleaner.

The presence of the reducing agent may stabilise the cross-linking process and result in a scaffold with enhanced biological efficacy. Furthermore, the presence of the reducing agent is likely to reduce the cytotoxic effects caused by the leaching of un-reduced cross-linking agent from the composition.

Examples of a suitable reducing agent include sodium borohydride or agents with similar carbonyl group reactivity. The reducing agent may typically be added in an amount of 0.1% w/v to 10% w/v (e.g. about 1% w/v).

The step of washing to remove agents involved in solubilising and/or cross-linking may be carried out for at least 5 hours, preferably at least 8 hours. For example, to remove oxalic acid and unbound glutaraldehyde, the scaffold may be washed with a reducing agent (such as sodium borohydride) for approximately 8 hours. Preferably, the scaffold is agitated or shaken whilst in contact with the reducing agent.

After contact with the reducing agent, there may be a further washing step, which may involve washing with water e.g. distilled water, and/or ethanol. This may help to remove any remaining unbound cross-linking agent or oxalic acid.

According to the invention, there is provided a method comprising:
a) solubilising elastin; b) cross-linking a composition comprising solubilised elastin obtained from step a); c) lyophilising a product from step b); and d) washing the product from step c).

According to the invention there is provided a method comprising:
a) solubilising elastin; b) cross-linking a composition comprising unfractionated, solubilised elastin obtained from step a); c) lyophilising the product from step b); and d) washing the product from step c).

According to the invention, there is provided a method comprising: a) contacting elastin with a solubilising agent that is able to solubilise the elastin; b) cross-linking the composition obtained from step a); c) lyophilising the product obtained from step b); and d) washing the product of step c).

After washing, the scaffold may be sterilised. In some embodiments, sterilisation involves washing the scaffold with ethanol and PBS.

According to the invention there is provided a method comprising: a) solubilising elastin; b) cross-linking the composition obtained from step a); c) lyophilising the product from step b); d) washing the product from step c); and e) sterilising the product from step d).

According to the invention there is provided a method comprising: a) solubilising elastin; b) cross-linking a composition comprising unfractionated, solubilised elastin obtained from step a); c) lyophilising the product from step b); d) washing the product from step c); and e) sterilising the product from step d).

According to the invention, there is provided a method comprising: a) contacting elastin with a solubilising agent; b) cross-linking the composition produced by a); c) lyophilising the product of step b); d) washing the product of step c); and e) sterilising the product of step d) Scaffolds of the invention are preferably sterile.

According to the invention, there is provided a tissue scaffold obtained or obtainable by a method according to the invention.

In some embodiments, scaffolds of the invention are not hydrogels.

It is envisaged that the methods and scaffolds of the invention may also be applicable to elastin derivatives or fragments, such as synthetic elastin sequence-based materials or elastin-like peptides (ELPs). ELPs are biopolymers based on key, repeating elastin sequences. For example, ELPs may have repeating peptides, such as pentapeptides or hexapeptides comprising Val, Gly and/or Pro. ELPs may possess the elastic properties of elastin using the pentapeptide repeat VPGXG where X is any amino acid besides praline (such as Val or Ile) (Zhang et al (2015), Daamen (2007)).

According to the invention, there may be provided a method comprising cross-linking elastin derivatives or fragments.

According to the invention, there may be provided a tissue scaffold comprising cross-linked elastin derivatives or fragments.

According to the invention, there may be provided a method comprising lyophilising cross-linked elastin derivatives or fragments.

According to the invention there may be provided a tissue scaffold comprising lyophilised cross-linked elastin derivatives or fragments.

Scaffolds of the invention may comprise other extracellular matrix components.

Scaffolds of the invention may comprise collagen. Consequently, according to the invention, there is provided a scaffold comprising elastin and collagen.

Scaffolds of the invention may comprise fibrin. Consequently, according to the invention, there is provided a scaffold comprising elastin and fibrin.

Scaffolds of the invention may comprise collagen and elastin. Consequently, according to the invention, there is provided a scaffold comprising elastin, collagen and fibrin.

Preferably, the elastin has been solubilised. Preferably the elastin is unfractionated, solubilised elastin. The elastin may be unfractionated. The elastin may comprise solubilised elastin. The elastin may comprise insoluble elastin.

Scaffolds of the invention may be formed by mixing a composition comprising elastin with a) a composition comprising collagen; and/or b) a composition comprising fibrin.

The composition containing collagen may comprise a collagen hydrogel. For example, a collagen hydrogel may be formed by standard procedures. The collagen hydrogel may be prepared using 80% rat tail collagen type I and 10× Minimal Essential Medium, neutralised using 5M and 1M sodium hydroxide and added 10× DMEM (Dulbecco's Modified Eagle Medium).

The composition containing fibrin may contain a fibrin gel. The fibrin gel may be formed by standard procedures. The fibrin gel may be prepared with 2% fibrinogen dissolved in 1 ml of PBS, then adding 1% thrombin with $0.1M$ $CaCl_2$.

According to the invention, there is provided a method comprising mixing a composition comprising elastin (preferably a composition comprising unfractionated, solubilised elastin) with a composition comprising collagen (preferably a collagen hydrogel), and/or a composition comprising fibrin (preferably a fibrin gel).

According to the invention, there is provided a composition comprising elastin (preferably unfractionated, solubilised elastin), collagen and/or fibrin. The composition may comprise a cross-linking agent.

The composition comprising elastin is preferably mixed with the composition comprising collagen and/or the composition comprising fibrin, prior to a cross-linking step. Consequently, the resulting scaffold may comprise cross-linked elastin, cross-linked collagen and/or cross-linked fibrin.

According to the invention, there is provided a composition comprising elastin; a solubilising agent for solubilising elastin; a cross-linking agent; and fibrin and/or collagen.

The cross-linking may proceed as already described herein. For example, the cross-linking agent may comprise glutaraldehyde and may be carried out in the presence of $CO_2$. The cross-linking agent may be added to the composition comprising the elastin, collagen and/or fibrinogen. Alternatively, the cross-linking agent may be added to the composition comprising elastin, the composition comprising collagen and/or the composition comprising fibrinogen, prior to mixing the compositions. For example, the composition comprising elastin may comprise the cross-linking agent. The concentration of the cross-linking agent in the composition comprising elastin may be at a level (e.g. 3% by volume) such that when the composition comprising elastin is mixed with the composition comprising collagen and/or the composition comprising fibrin, the concentration is at a desirable level for cross-linking to take place (e.g. about 1% v/v).

Prior to cross-linking, the composition may be cast, as described herein.

Once the cross-linking has taken place, the scaffold may be lyophilised and/or washed, as described herein.

The relative amounts of elastin, collagen and/or fibrinogen may be adjusted to impart different architectural, mechanical and biodegradation properties to the resulting scaffold. For example, scaffolds containing higher proportions of elastin may result in denser structural networks, greater elasticity and delayed degradation compared to scaffolds with lower proportions of elastin. Increasing the amount of fibrin may increase the mechanical strength and accelerate the biodegradation rate. Increasing the amount of collagen may also accelerate the biodegradation rate. Using particular combinations of elastin, collagen and/or fibrinogen may also allow enhancement of angiogenic properties of the scaffold.

According to the invention, there is provided a tissue scaffold according to the invention for use as a medicament.

According to the invention, there is provided a method of promoting tissue healing, regeneration or repair comprising applying a tissue scaffold according to the invention, to a patient. For example, the scaffold may be used in wound healing or tissue grafts (such as skin grafts). The scaffolds of the invention may be particularly applicable to soft tissue regeneration or repair, such as skin regeneration or vascular tissue regeneration. For instance, scaffolds may be used in adipose, skin, vascular grafts, heart valves or lung tissue engineering.

According to the invention, there is provided a tissue scaffold according to the invention, for use in promoting tissue healing, regeneration or repair.

According to the invention, there is provided use of a tissue scaffold according to the invention, in the manufacture of a medicament for promoting tissue healing, regeneration or repair The invention may provide a method substantially as described herein with reference to the figures.

The invention may provide a tissue scaffold substantially as described herein with reference to the figures.

According to the invention, there is provided a scaffold as described herein, seeded with cells. The scaffold may be in vitro or ex vivo. The cells may be stem cells, such as human adipose-derived stem cells (hADSCs).

According to the invention, there is provided a method comprising seeding a scaffold of the invention with cells.

According to the invention, there may be provided a cell or tissue culture comprising a scaffold as defined herein.

Scaffolds of the invention may have a mean pore size less than 120 µm. Scaffolds of the invention may have a mean pore size less than 100 µm, Scaffolds of the invention may have a mean pore size of 10 µm or greater. Scaffolds of the invention may have a mean pore size of 20 µm or greater. For instance, scaffolds of the invention may have a mean pore size of 10 to 120 µm. Scaffolds of the invention may have a mean pore size of 20 to 100 µm.

The pore size distribution may be altered by including collagen and/or fibrin with elastin, or by changing the relative amounts of each component (see, for example, FIGS. 14 and 15).

Scaffolds of the invention may have a modal pore size of 80 µm or less. For example, the modal pore size may be 60 µm or less. The modal pore size may be 1 µm or greater, for example 10 µm or greater, or 20 µm or greater. For instance, the modal pore size may be in the range of 1 to 80 µm, for example 1 to 60 µm, 20 to 60 µm, or 1 to 60 µm.

In one example, the modal pore size may be in the range of 1-20 µm. In another example, the modal pore size may be in the range of 20 to 40 µm. In one embodiment, the modal pore size may be in the range 40 to 60 µm.

Characteristics of scaffolds such as pore size and porosity may be calculated using appropriate readily-available software. For example, ND ("Nearest Distance") is an ImageJ plugin that was developed to calculate the average size and distance between pores and their nearest neighbours in porous scaffolds (see Haeri et al. (2015)). DiameterJ is another example of an ImageJ plugin that can be used to measure pore parameters. Microscopic images of the scaffold (e.g. SEM images) may be used as input.

The total porosity of scaffolds of the invention may be at least 25%. For example, the total porosity may be at least 40%.

Examples of the invention are now described by way of example only, with reference to the accompanying drawings, in which:

FIG. 1 shows elastin scaffold fabrication process from insoluble elastin (A), mixed with 0.5M oxalic acid (B), crosslinked with 1% GTA and incubated at 37° C. for 1 hour (C), frozen at −80° C. overnight (D), and lyophilised for 48 hours (E);

EXAMPLE 1—ELASTIN SCAFFOLDS

Fabrication Method and Materials

Figure 1:
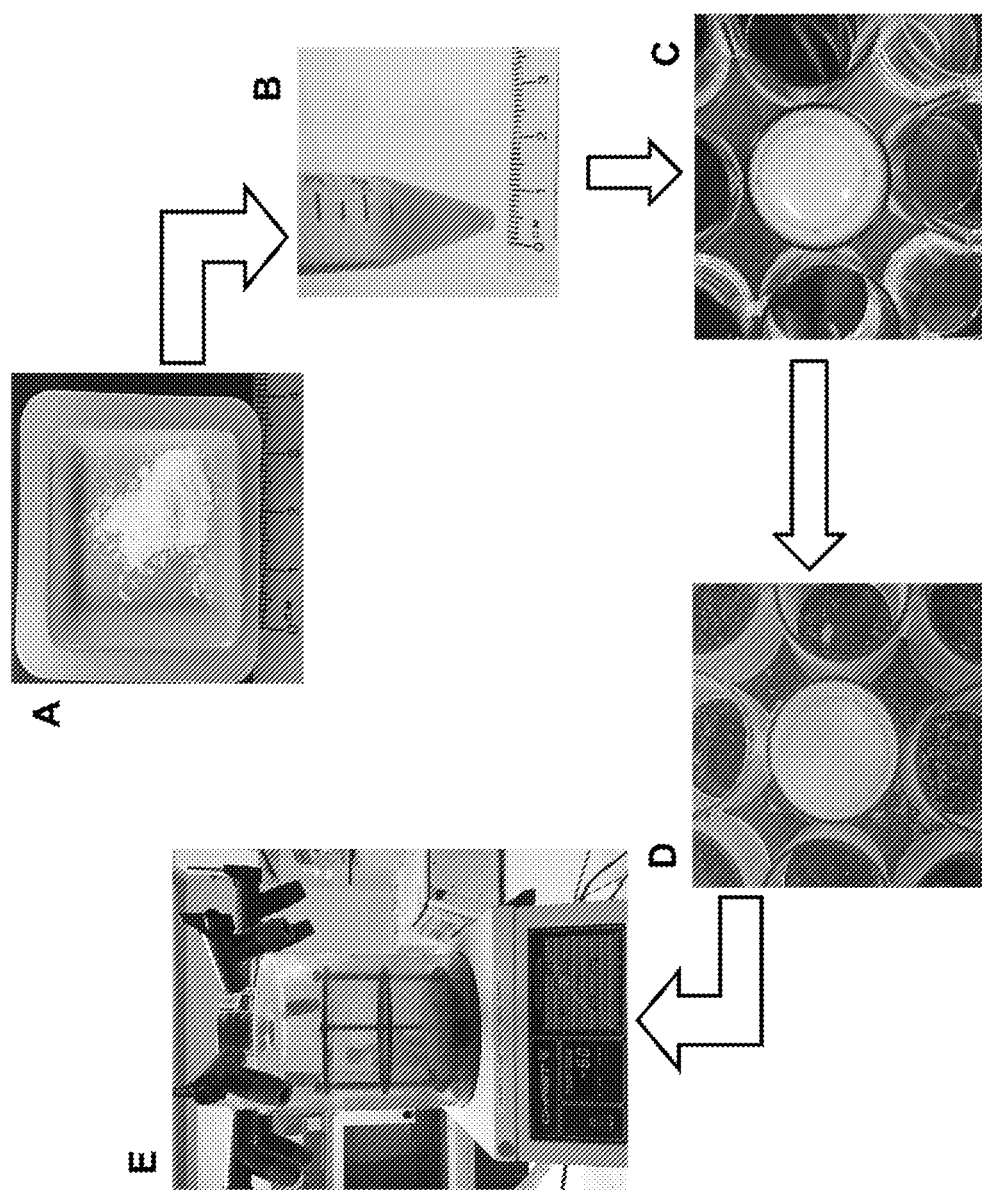
FIG. 1 shows scaffolds fabricated without crosslinking agent (A), or with cross-linking agent (B)

Insoluble elastin powder was obtained from Sigma (the source of elastin was derived from bovine neck ligament) (FIG. 1A). 100 mg of insoluble elastin powder was mixed with 1 ml of 0.5M oxalic acid ($C_2H_2O_4$) (freshly prepared) at room temperature (FIG. 1B).

To cross-link the protein, a homobifunctional cross-linking agent, 1% glutaraldehyde (GTA) (v/v), was added to the solution (FIG. 1C). The solution was cast in a well of a 24 well plate and incubated at 37° C. with 5% $CO_2$ for one hour (FIG. 1C).

The mixture was frozen at −80° C. overnight (FIG. 1D) and lyophilised for 48 hours to form a scaffold (FIG. 1E).

The fabricated scaffold was brought to room temperature and washed with 0.1M Glycine buffer at pH=10.4 with 2 washes of 15 minutes each and washed with tris-glycine buffer for 15 minutes. To remove excess of oxalic acid and unbound glutaraldehyde, scaffolds were washed with 0.1% w/v sodium boro-hydride ($NaBH_4$) a reducing agent for approximately 8 hours on a shaker.

Subsequently, scaffolds were washed with distilled warm water (60° C.) for 15 minutes and two washes of distilled water for 30 minutes each to remove remaining unbound glutaraldehyde from the scaffold.

For sterilisation, scaffolds were washed with 70% ethanol for 15 minutes and then with PBS.

Structural Integrity and Stability

The fabricated crosslinked elastin scaffold was intact (FIG. 2B). However, the non-crosslinked scaffold was dismantled/disintegrated (FIG. 2A).

Figure 3:
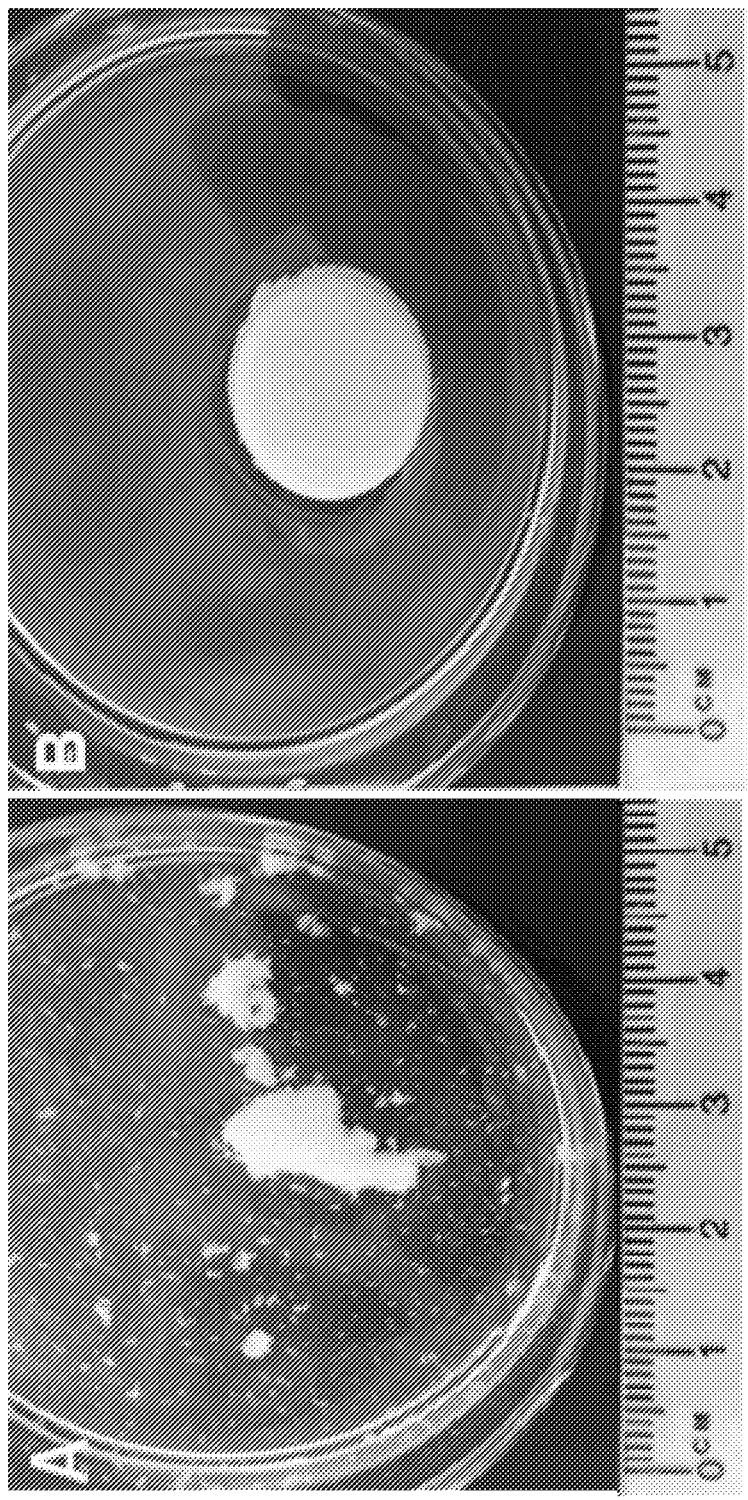
FIG. 3 shows a live/dead assay at 1(A), 3 (B) and 7 (C) days for adipose derived stem cells (ADSC) growing on the scaffolds, with green points indicating alive cells.
Figure 4:
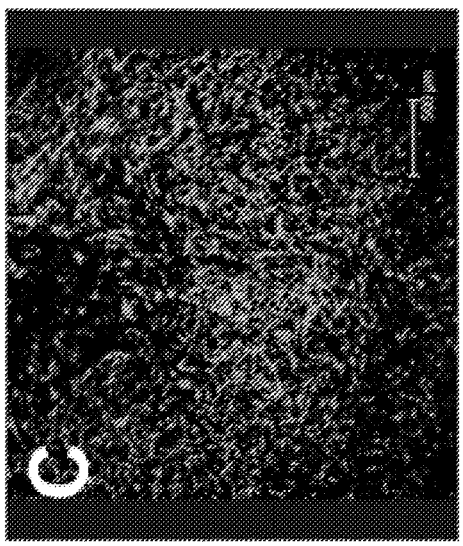
FIG. 4 shows a cell proliferation assay using alamar blue at 1, 3 and 7 days.
Figure 4:
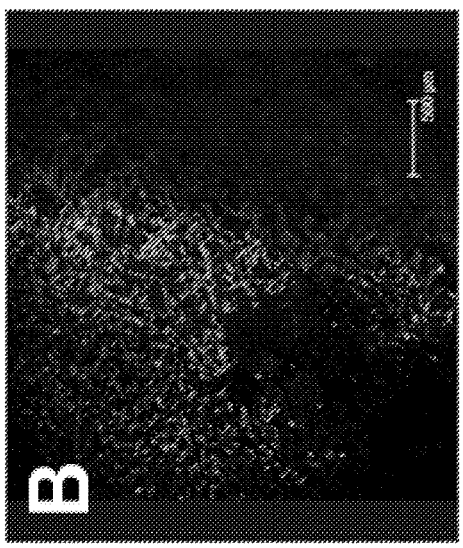
Figure 4:
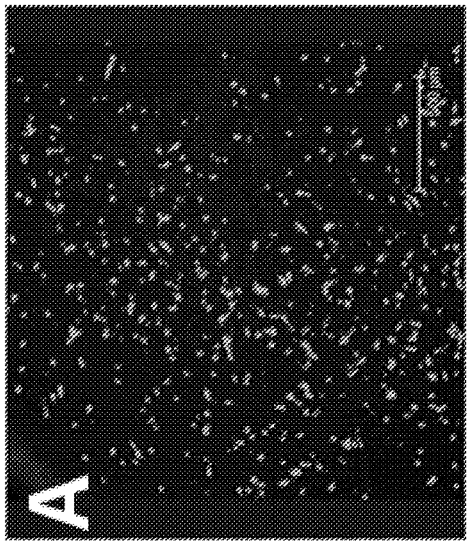

An in vitro scaffold stabilisation study was carried out by comparing scaffolds with and without cross-linking for 28 days in PBS at 37° C. and 5% $CO_2$. It was found that non-crosslinked scaffolds (FIG. 3A) were dismantled/disintegrated after 28 days in PBS and in contrast crosslinked scaffolds were intact (FIG. 3B). This indicates that this method of fabrication effectively produced an integral scaffold, Biological Activity To evaluate the efficacy and biological activity of the scaffolds, adipose-derived stem cells (ADSCs) were cultured under standard culture conditions i.e. incubation at 37° C. with 5% $CO_2$ in MesenPRO RS™ basal cell culture medium (ThermoFisher, UK) supplemented with 2% MesenPRO RS™ growth supplement (ThermoFisher, UK) and 1% penicillin/streptomycin (Sigma-Aldrich, UK). 50000 cells were seeded on 6 mm diameter scaffolds and cultured for 1, 3 and 7 days. Cell survival and proliferation were studied using live/dead and alamar blue assays respectively. ADSCs were alive and adhered to the scaffold by day 1 and exhibited non-aggregated morphology on days 3 and 7 (FIG. 4). Additionally, cells maintained their non-aggregated behavior and demonstrated spindle morphological structure (FIG. 4) suggesting they retain their stem characteristics during the culture period.

Figure 5:
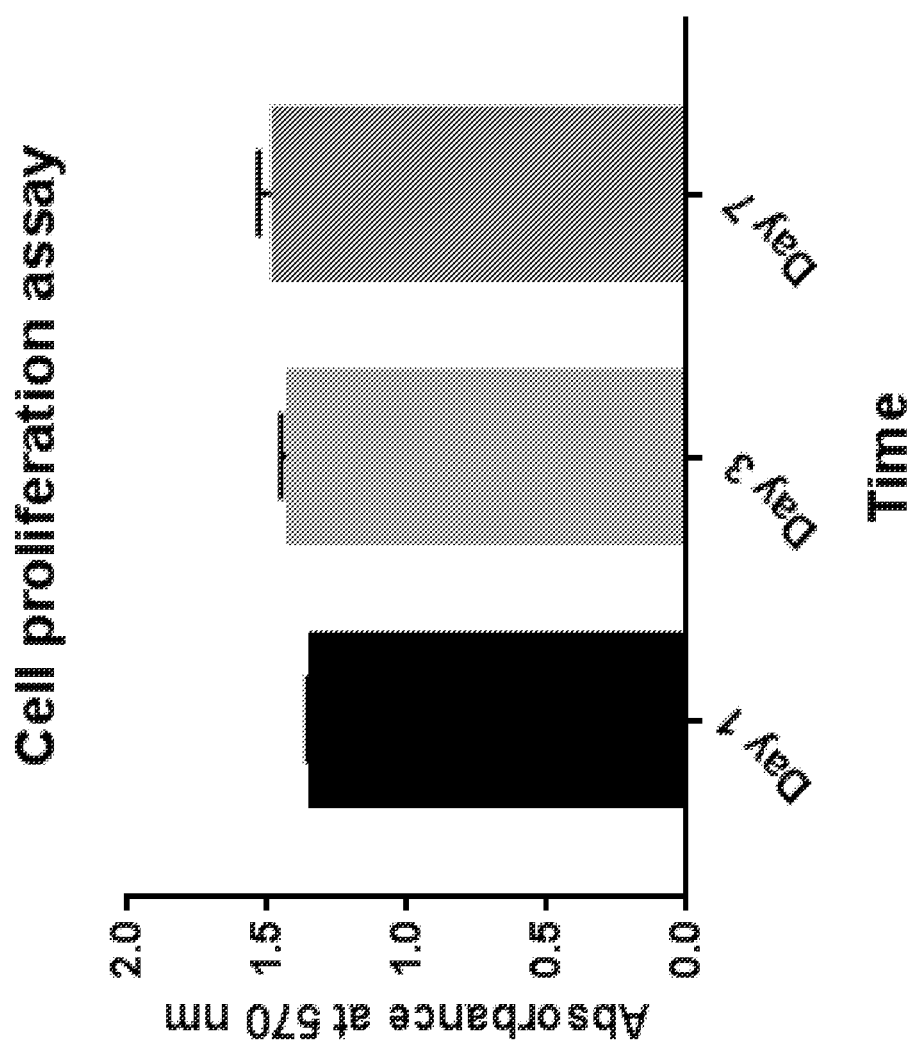

Cell proliferation was quantitatively measured by alamar blue activity, a cell metabolic assay, and the absorbance at 570 nm was measured using a spectrophotometer at days 1, 3, and 7 (n=3 per time point) (FIG. 5).

Scanning Electron Microscopy

Elastin scaffolds were washed with distilled water in an ultra-sonic cleaner for 3 minutes to remove salts and dried for 24 hours in a lyophiliser. Scaffolds were mounted on stubs and sputter-coated with carbon under vacuum. All images were obtained using a secondary electron detector in a Philips XL 30 Field Emission SEM, operated at 5 kV and average working distance was 10 mm.

Figure 2:
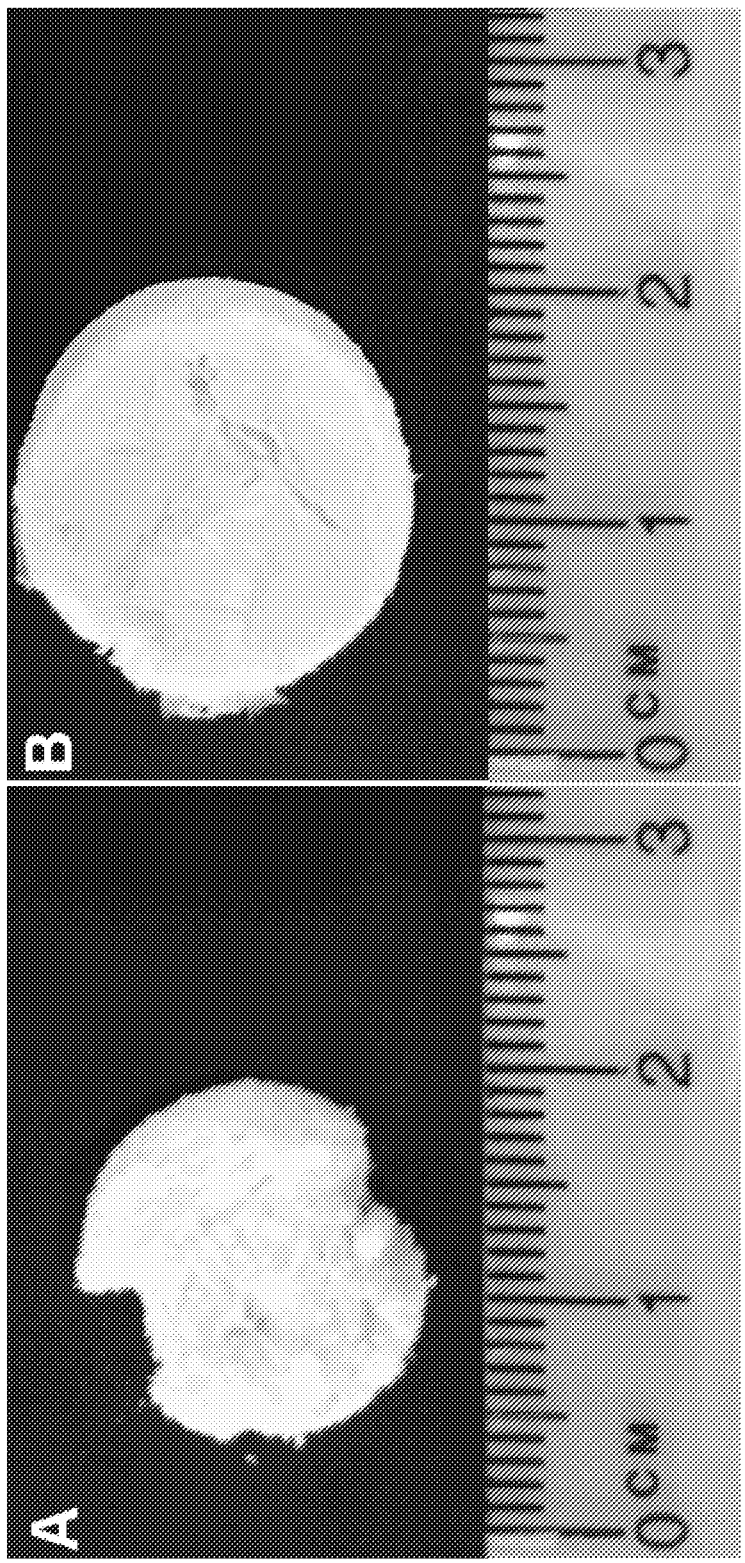
FIG. 2 shows a scaffold stabilisation study without cross-linking agent (A), and with crosslinking agent (B) after 28 days in PBS.
Figure 6:
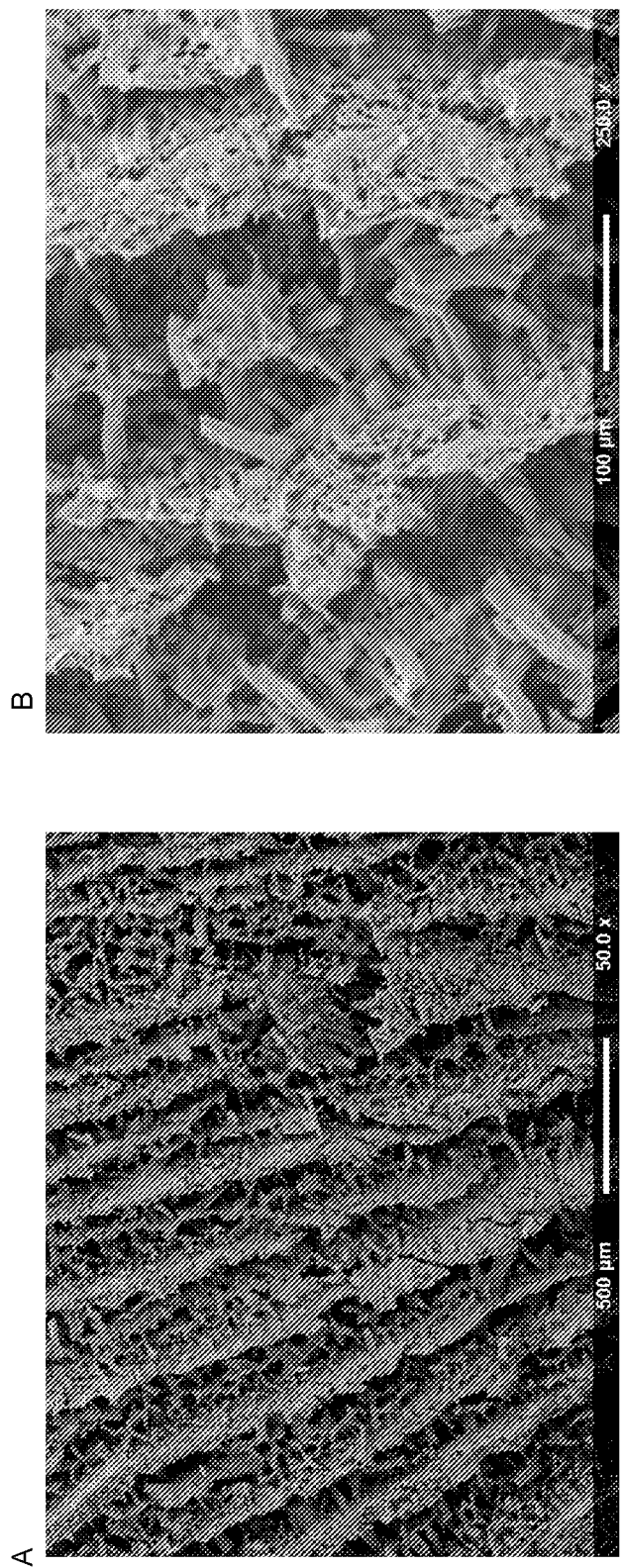
FIG. 6 shows scanning electron microscopy (SEM) images of elastin scaffolds.

The SEM images in FIGS. 6A and 6B show that elastin scaffolds have an homogeneous structure and are porous in nature. FIG. 6A is at 50× magnification and FIG. 2 is at 250× magnification.

Discussion

This is a very cost-effective and time-efficient way to fabricate elastin scaffolds because, as of the priority date of this application, 5 mg of insoluble elastin from bovine neck ligament cost £69.70 GBP (E1625) whereas 1 mg of soluble α-elastin costs £272.50 GBP (E6527) from Sigma™ as the commercial supplier.

The live/dead assay results showed that cells maintained their spindle morphological structure which is one of the characteristics of ADSCs. Since ADSC have contact inhibition behavior (Majd et al., 2011) by using an elastin scaffold within the scope of the invention, the inventors were able to maintain contact inhibition behavior up to day 7 (FIG. 4). This cell morphology can maintain ADSCs phenotype and multipotent characteristics without undergoing any differentiation (Zhang and Kilian, 2013). An increase in the alamar blue absorbance is an indication of constant cell proliferation. These results also show that the fabricated scaffold was non-toxic to the cells.

EXAMPLE 2—ELASTIN/COLLAGEN/FIBRIN SCAFFOLDS

Figure 7:
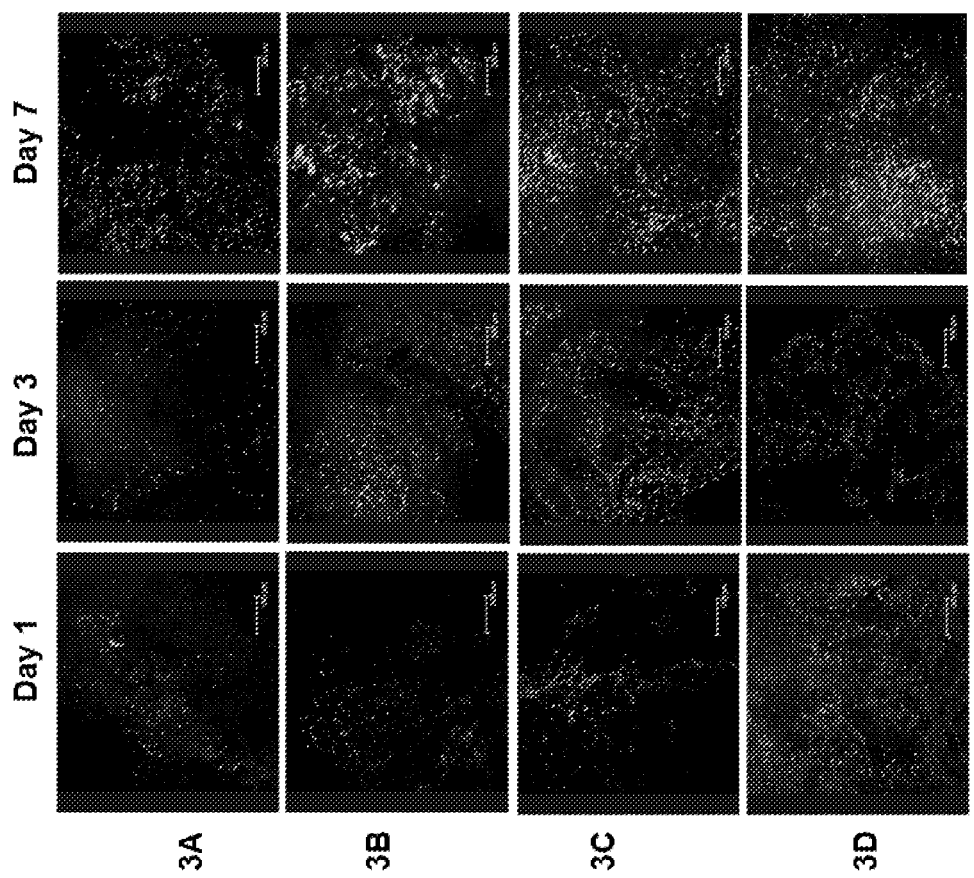
FIG. 7 shows live/dead assay on days 1, 3 and 7 for different combination scaffolds (3A=Collagen/Elastin/Fibrin 2:1:1; 3B=Elastin/Collagen/Fibrin 2:1:1; 3C=Fibrin/Collagen/Elastin 2:1:1; 3D=Fibrin/Collagen/Elastin 1:1:1)
Figure 8:
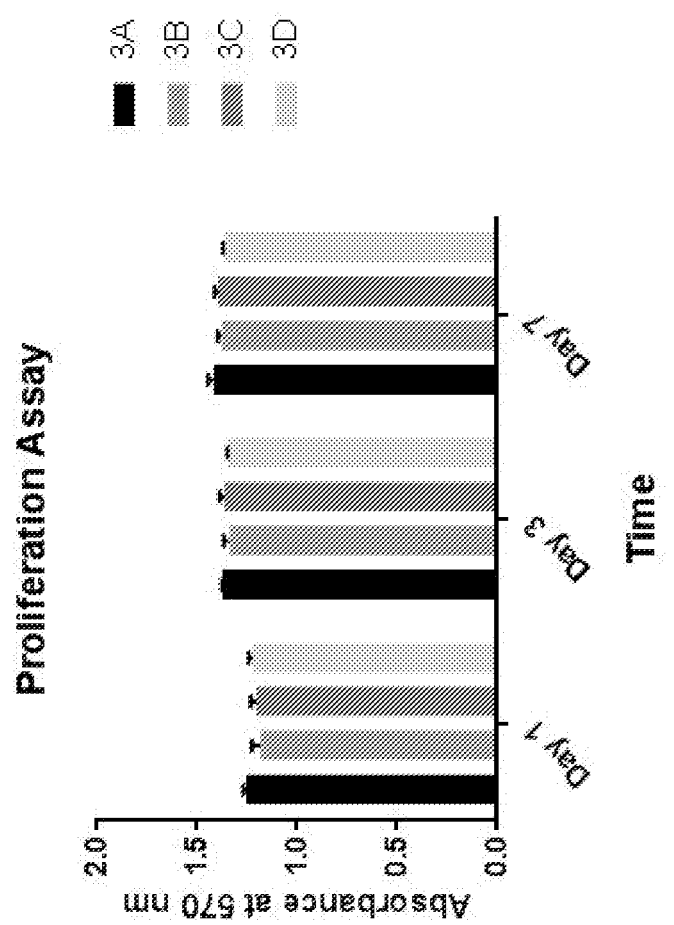
FIG. 8 shows a cell proliferation assay (alamar blue activity) for combination scaffolds (3A=Collagen/Elastin/Fibrin 2:1:1; 3B=Elastin/Collagen/Fibrin 2:1:1; 3C=Fibrin/Collagen/Elastin 2:1:1; 3D=Fibrin/Collagen/Elastin; 1:1:1)
Figure 9:
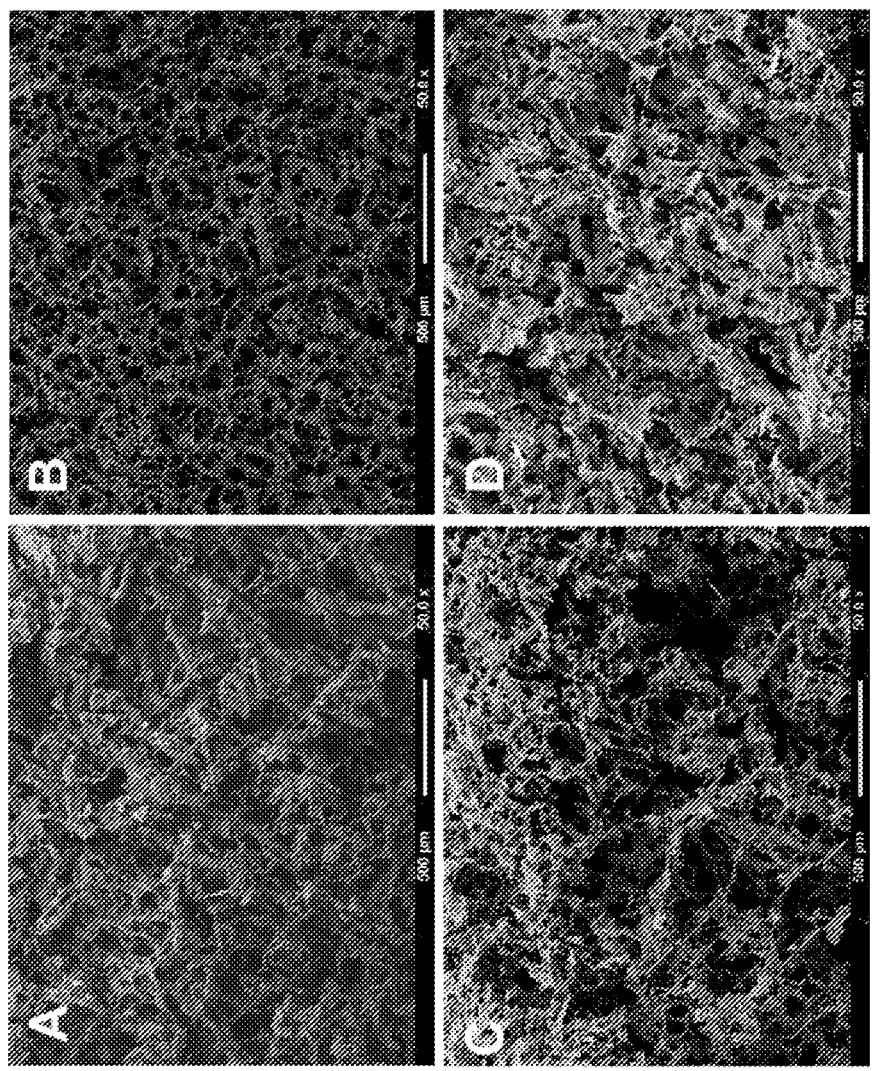
FIG. 9 shows SEM Images illustrating differences in fibril network and pore structure of each individual combination, A) 3A=Collagen/Elastin/Fibrin 2:1:1, B) 3B=Elastin/Collagen/Fibrin 2:1:1, C) 3C=Fibrin/Collagen/Elastin 2:1:1, D) 3D=Fibrin/Collagen/Elastin 1:1:1.

Fabrication Method and Materials
Tube 1: Elastin powder (9.7% w/v)+0.5M oxalic acid+3% glutaraldehyde (w/v).
Tube 2: Collagen hydrogel—prepared using 80% rat tail collagen type I (v/v) (First Link, Birmingham, UK) and 10% of 10× Minimal Essential Medium (Invitrogen, Paisley, UK), neutralised using 5M and 1M sodium hydroxide (Sigma-Aldrich, Dorset, UK) and added 10× DMEM.
Tube 3: Fibrin gel—prepared with 2% fibrinogen (w/v) dissolved in 1 ml of PBS and for fibrillogenesis, 1% thrombin (w/v) was added along with 0.1M CaCl2
Tubes 1 to 3 were mixed in varying ratios, cast and then incubated at 37° C. with 5% $CO_2$ for 1 hour. The final volume after mixing the 3 tubes was always 1 ml, which was then cast.
For scaffolds that were 2:1:1 (collagen/elastin/fibrin), 500 µl of Tube 2 were mixed with 250 µl of Tube 1 and 250 µl of Tube 3 (Also referred to herein as scaffold 3A).
For scaffolds that were 2:1:1 (elastin/collagen/fibrin), 500 µl of Tube 1 was mixed with 250 µl of Tube 2 and 250 µl of Tube 3 (Also referred to herein as scaffold 3B).
For scaffolds that were 2:1:1 (fibrin/elastin/collagen), 500 µl of Tube 3 were mixed with 250 µl of Tube 1 and 250 µl of Tube 2 (Also referred to herein as scaffold 3C).
For scaffolds that were 1:1:1, 333.3 µl of each tube were mixed and cast (Also referred to herein as scaffold 3D).
The mixture was freeze-dried for 48 hours.
Washing: First, a wash for 15 minutes with tris-glycine buffer. Second, to remove excess and unbound glutaraldehyde, scaffolds were washed with 0.1% sodium boro-hydride ($NaBH_4$) a reducing agent for approximately 8 hours on a shaker.
Biocompatibility
To evaluate biocompatibility of each combination scaffold, 50000 adipose derived stem cells (ADSC) were seeded per scaffold and cultured up to 7 days. Cell survival and proliferation at 1, 3 and 7 days after seeding were studied using live/dead and alamar blue assays respectively.
As an example, results for the three-component scaffolds show that ADSC were alive and adhered to the scaffold (FIG. 7) and were proliferating until day 7 (FIG. 8). The same results were observed in two-component scaffolds (i.e. scaffolds comprising elastin and collagen, or elastin and fibrin).
Microstructure
Microstructure of each scaffold was studied using SEM. Results for three-component scaffolds (FIG. 9) showed that each scaffold combination has a unique ultrastructural fibril network and pore size. Similar observations were made for two-component scaffolds. This variation in the structure could alter ADSC behaviour and differentiation as well as biomechanical properties of the scaffolds (See Ghasemi-Mobarakeh et al (2015)).

EXAMPLE 3—WATER CONTACT ANGLE (WCA)

Figure 10:
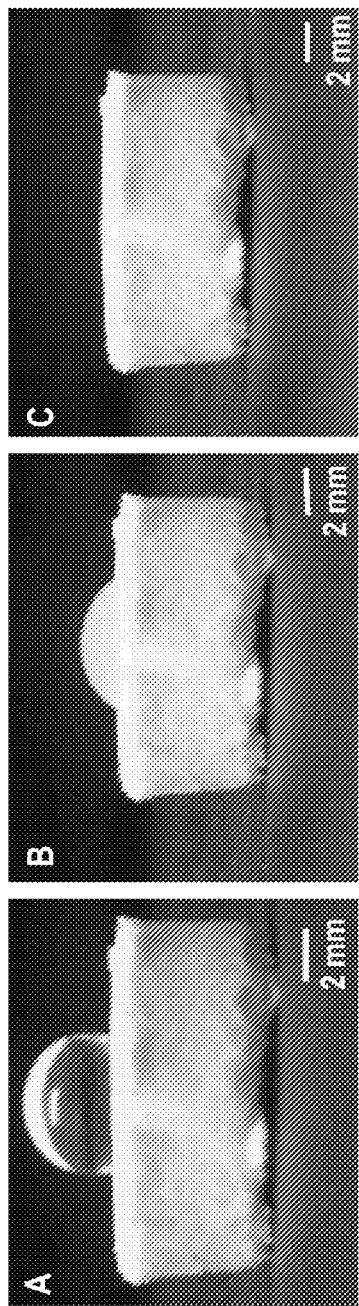
FIG. 10 shows wettability of elastin scaffolds at 0 seconds (A), 4 seconds (B), 9 seconds (C) and water contact angle measurement per second (D)
Figure 10:
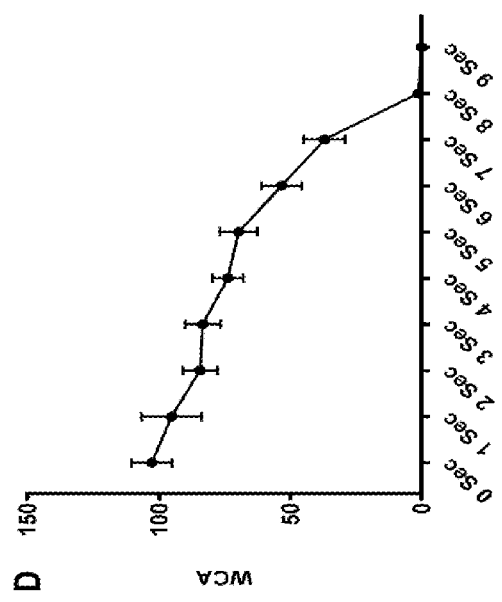
Figure 11:
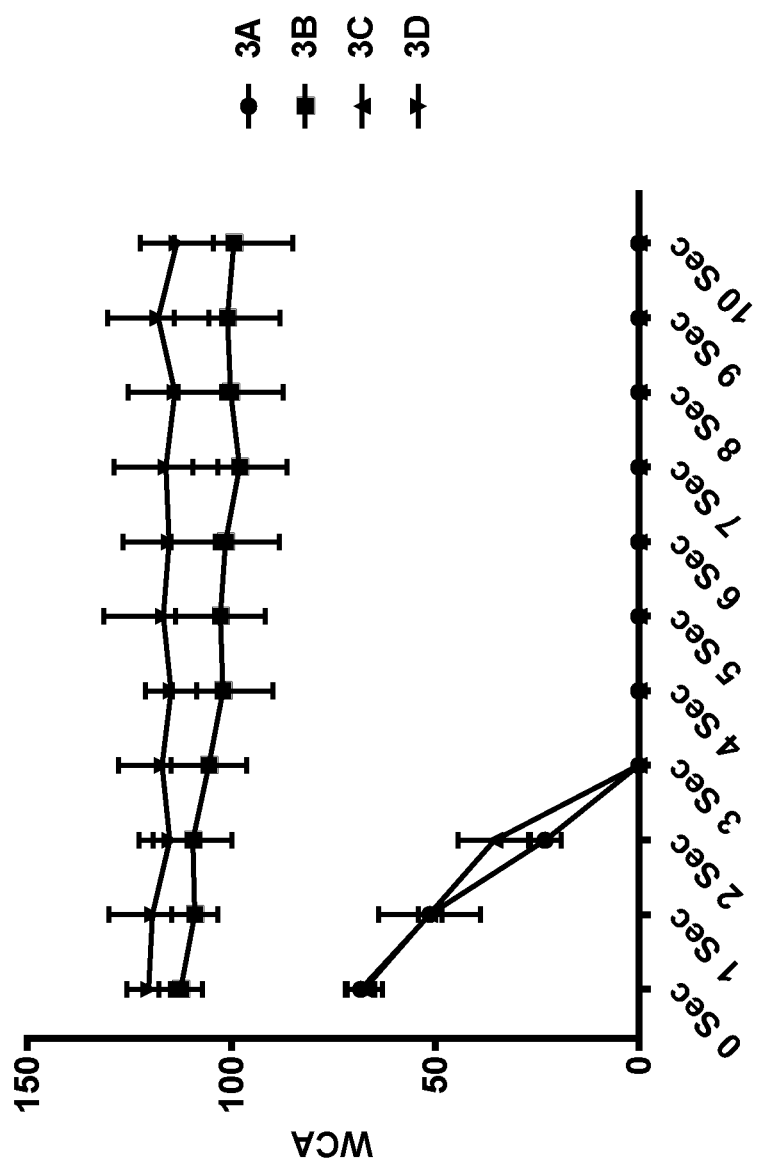
FIG. 11 shows water contact angle measurements per second for elastin-based scaffolds.

The wettability of the elastin scaffold was investigated by developing an experimental setup and a 30 µL distilled water droplet was dispensed onto each scaffold and several images were taken over the time interval between 0 to 5 seconds. The time at 0 seconds was considered the initial time of contact with a liquid medium (water). The WCA was calculated using Young's equation and the angle was measured from the water-scaffold interface to the line tangent and perimeter of the water droplet (Fu et al (2014)). The calculated WCA is a demonstration of water-material interaction.
The calculated WCA for elastin at 0 seconds was 102±7.75° and it was reduced to 73.88±5.90° at 4 seconds. Over the time WCA continued to decrease over time and at reached 0° at 9 seconds which indicated complete wettability of the elastin scaffold (FIG. 10).
However, by combining elastin with other natural polymers such as fibrin and collagen at different ratios the WCA for 3A (68.18±3.38° at 0 seconds to 0° at 3 seconds), 3C (67.46±4.51° at 0 seconds to 0° at 4 seconds) was altered and showed complete wettability by 4 seconds. Interestingly WCA for 3B (112.34±5.37° at 0 seconds to 99.32±14.55° at 10 seconds) and 3D (120.18±5.36° at 0 seconds to 113.23±8.93 at 10 seconds) (FIG. 11) did not show complete wettability even at 10 seconds making them hydrophobic as for any material >90° is considered to be hydrophobic therefore elastin, 3A and 3C scaffolds demonstrated hydrophilic nature and showed high cohesion towards water and gained complete wettability by 9 seconds. but scaffolds 3B and 3D showed to hydrophilic nature with low cohesion towards the water.

EXAMPLE 4—ACCELERATED TRYPSIN DEGRADATION

Figure 12:
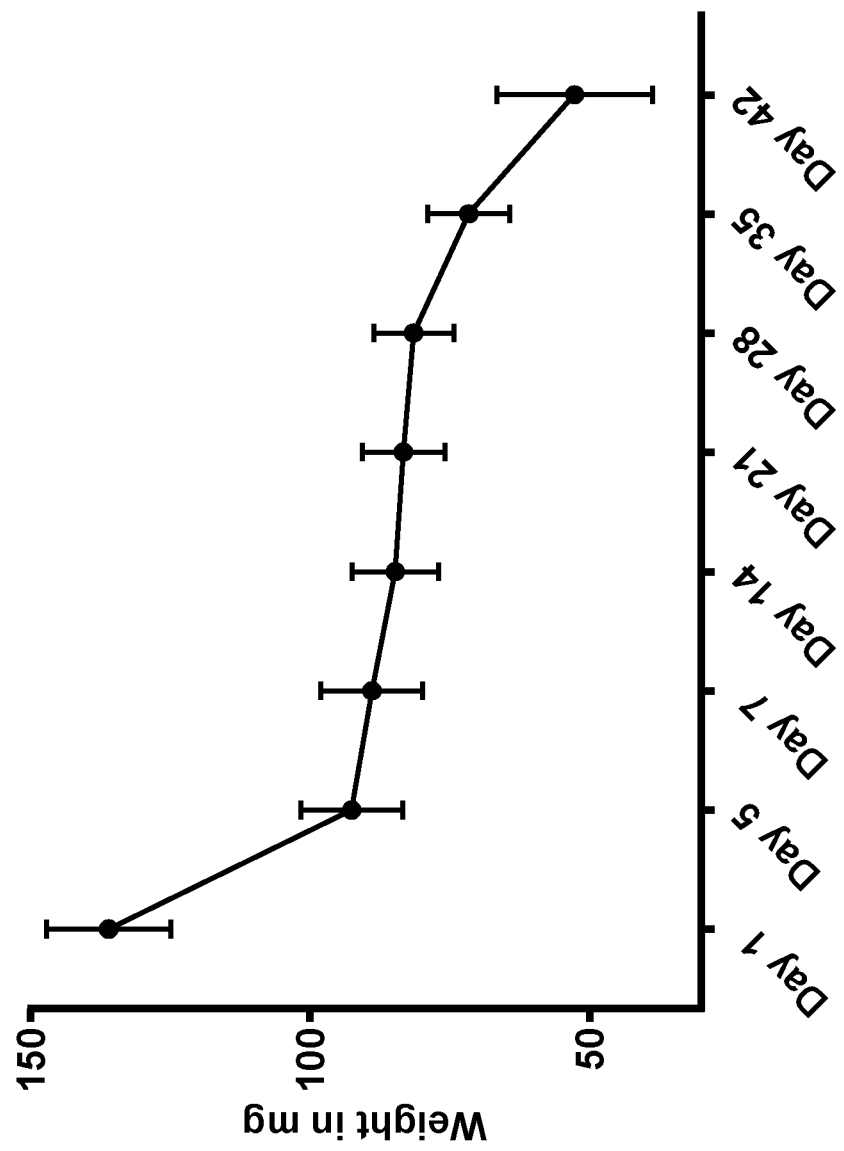
FIG. 12 shows an accelerated degradation profile of an elastin scaffold over a period of time.
Figure 13:
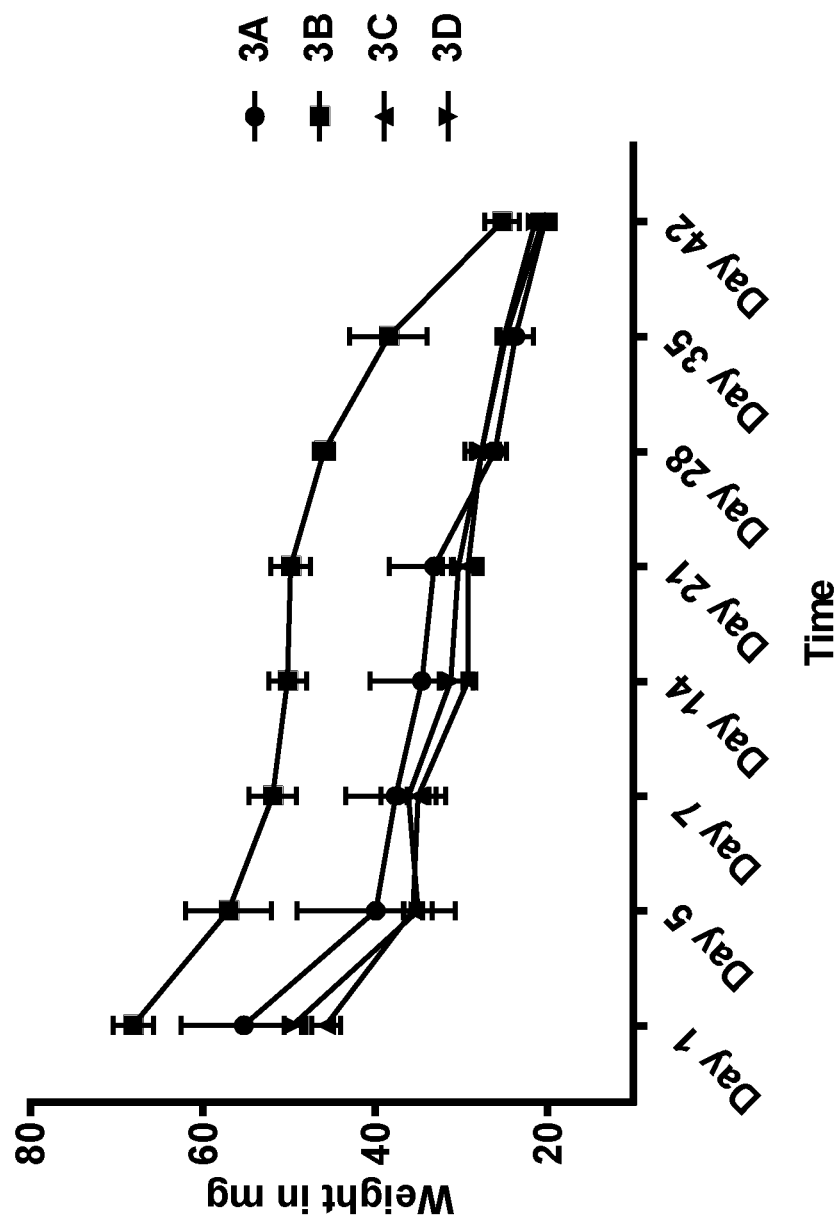
FIG. 13 shows accelerated degradation profiles of elastin-based composite scaffolds.

To measure the stability of scaffolds, an accelerated degradation profile was carried out by using 1× trypsin. An initial weight of scaffolds was measured using XS205 Mettler Toledo® digital scale. The scaffolds were placed in 24 well-plate with 1× trypsin and incubated at 37° C. and with 5% $CO_2$. At each time point, scaffolds were washed with distilled water and lyophilised and weight was measured.
A net change in the weight was measured as a parameter of the degradation. In vitro accelerated degradation results indicated that elastin scaffold degraded from day 1 (136.06±11.90 mg). By the day 5, there was 25% decrease in the weight and this trend continued and by day 42 there was 70% degradation of the scaffold (FIG. 12).
The degradation profile for the elastin-based co-polymers was identical for 3A, 3C and 3D. By day 7 almost 40% scaffolds were degraded this pattern was continued until day 42 where almost 70% of scaffolds were degraded. However, 3B, which has 50% of elastin, was the most stable scaffold with 55% degradation until day 42 (FIG. 13). This shows that different degradation pattern of elastin-based scaffolds can be used for various tissue engineering application depending upon regenerative properties of each tissue type.

EXAMPLE 5—STRUCTURAL PROPERTIES

To measure pore size range and porosity, all SEM images were quantitively analysed using ImageJ bundled with 64-bit Java 1.6.0 (NIH, USA). A threshold function was used to visualise all pores in the scaffold. Additionally, friction area, particle analysis function was used.

Figure 14:
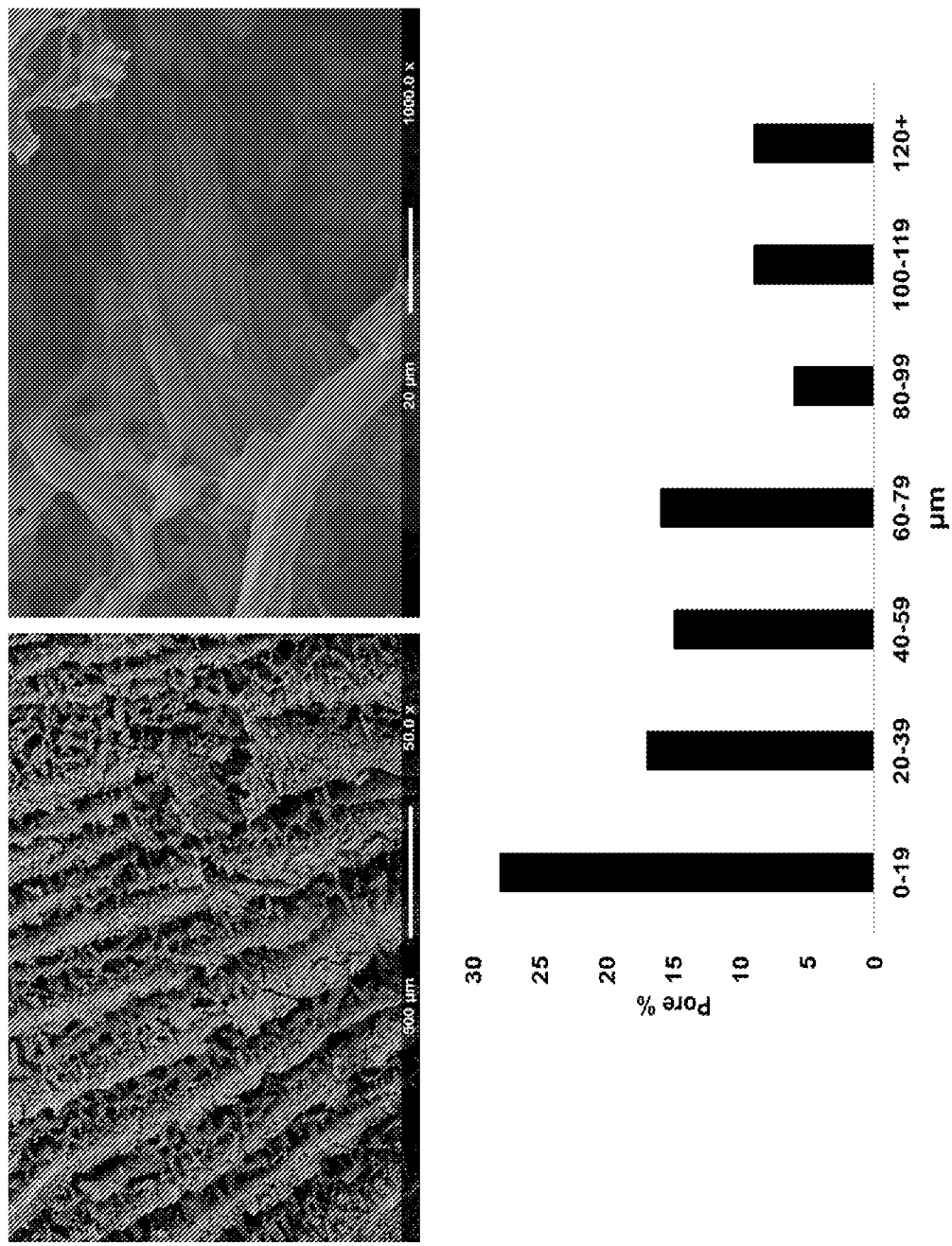
FIG. 14 shows SEM images of elastin scaffolds (50× and 1000×) and pore % from 0-120+µm.

Calculated pore size percentages for the scaffolds were in the range of 0-120+μm and 28% pores were in the range of 0-19 μm, 48% pores in the range of 20-79 μm and remaining 24% in the range of 80-120+μm (FIG. 14) and total porosity of scaffold was 48%.

Figure 15:
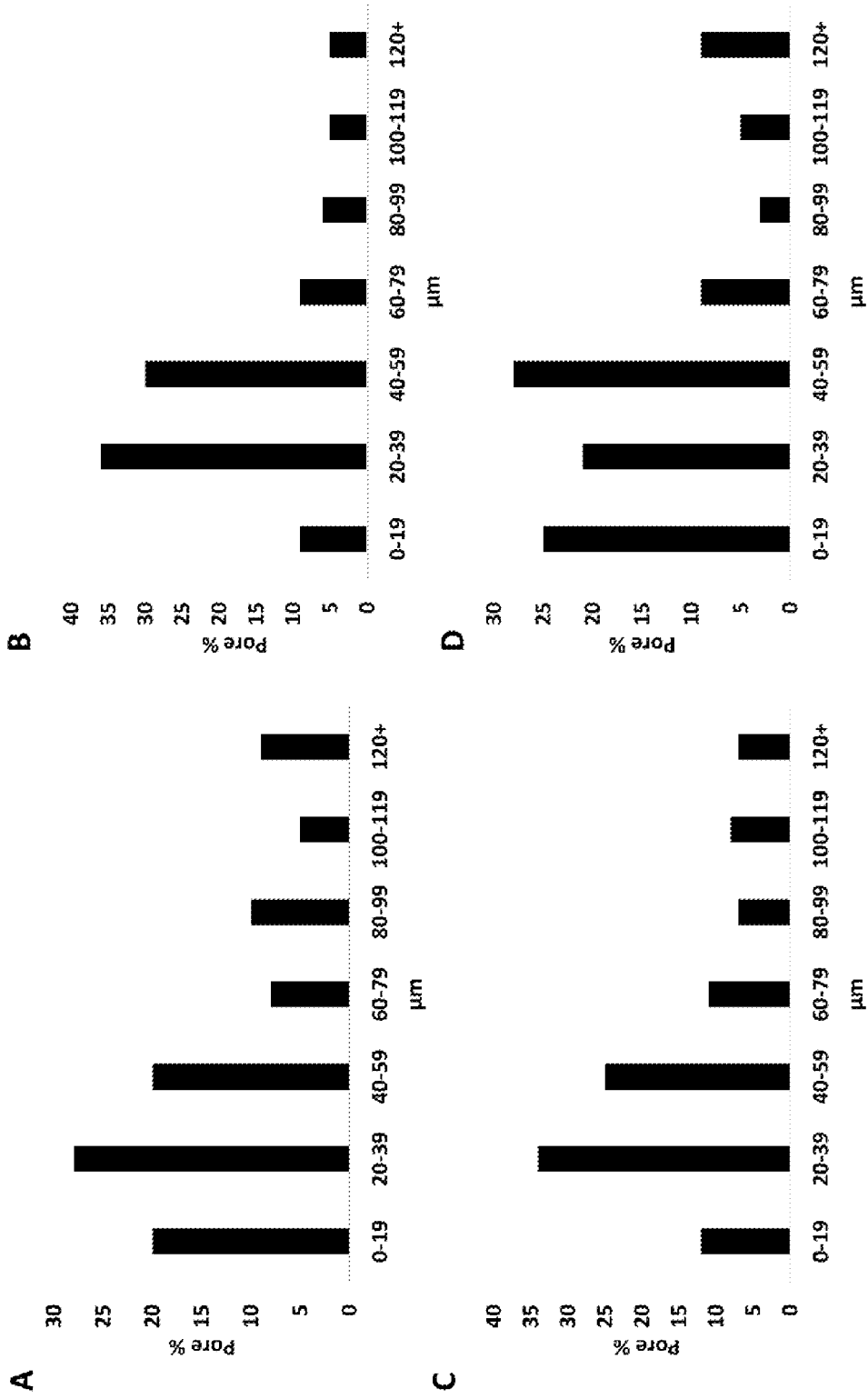
FIG. 15 shows pore size pattern for elastin-based composite scaffolds.

When elastin was combined with other polymers, 70% pores were present in the 0-59 and remaining 50% in the range of 60-120+μm in 3A. In 3B, the majority of pores (65%) were in the range of 20-59 μm but in 3C pore pattern was uniform and 55% pores were in the range of 20-59 μm. However, in 3D 75% pores were in the 0-59 μm range (FIG. 15).

Pore and porosity play a vital role in the angiogenesis and diffusion of nutrients. The results suggest that elastin-based scaffolds could be used for various tissue engineering applications.

EXAMPLE 6—MECHANICAL PROPERTIES

The elastin scaffold was tested to failure using bi-axial BioTester (CellScale Biomaterials Testing, Canada). The system includes 2 high-performance actuators with temperature-controlled media bath to avoid scaffold drying while testing cell-seeded scaffolds. To analyse real-time stress distribution, a time synchronised high-resolution CCD camera for the acquisition and processing of the test results was used.

Figure 16:
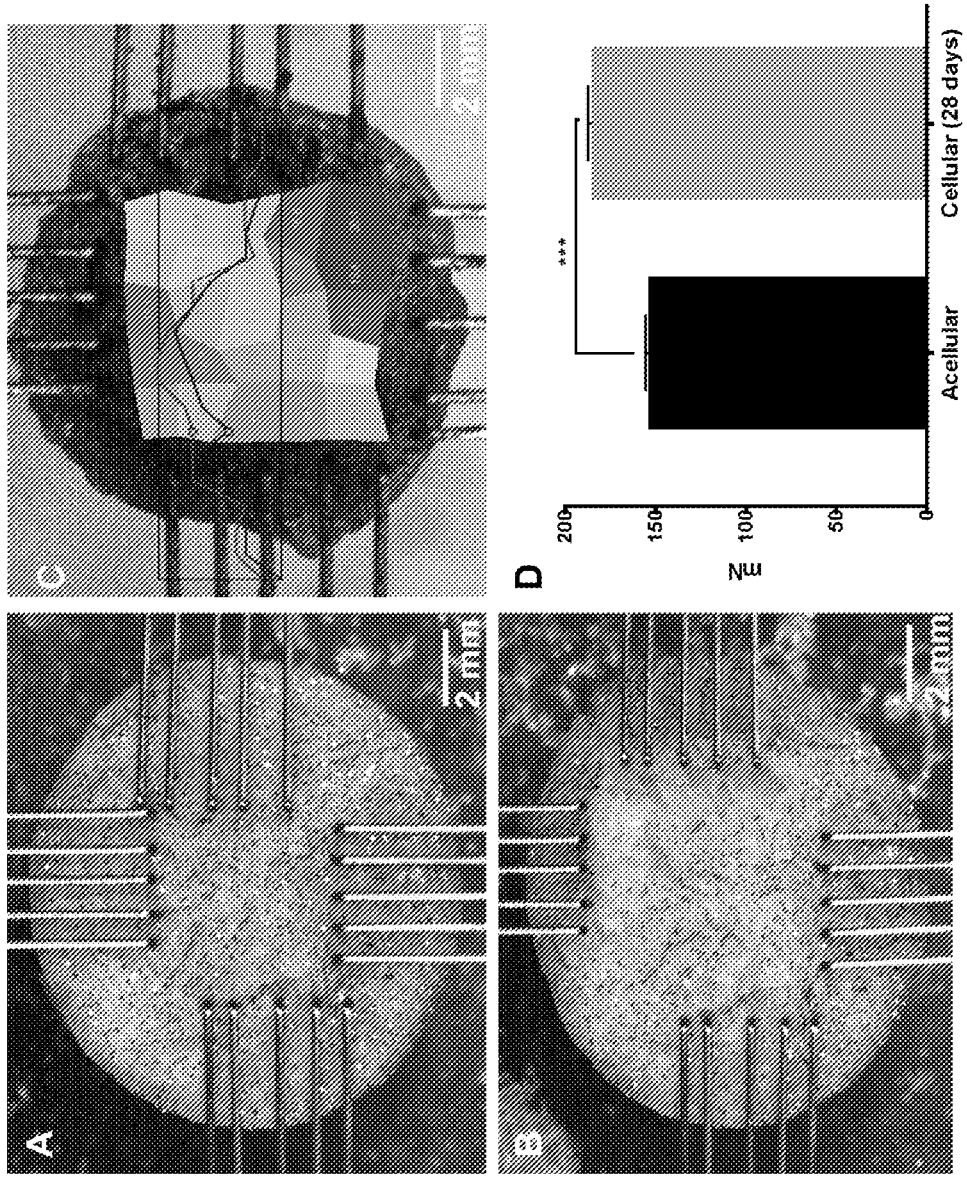
FIG. 16 shows mechanical testing of anelastin scaffold: pre-test scaffold (A), post-test scaffold (B), stress distribution on the scaffold (C) and break strength of the elastin scaffold (D) (*** denotes the statistical significance of p<0.0001)
Figure 17:
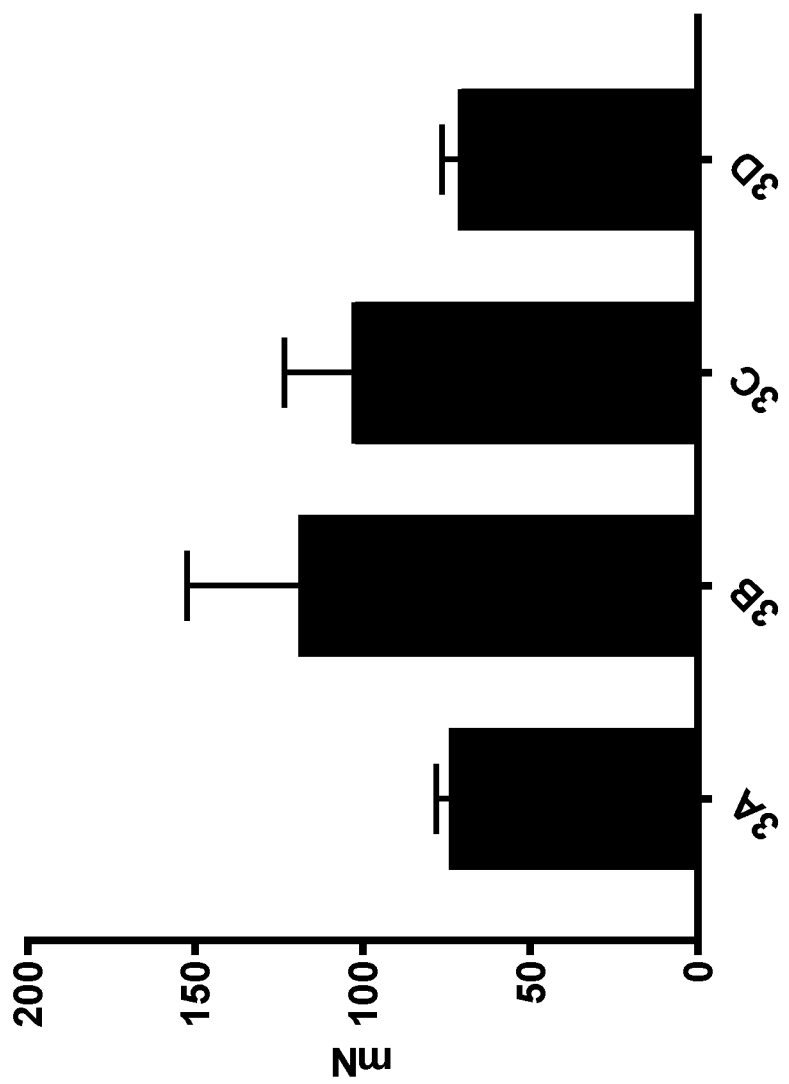
FIG. 17 shows mechanical properties for elastin-based composite scaffolds.

The wet mechanical properties of elastin scaffold at day 0 was 154±1 mN and after seeding hADSC cells for 28 days the strength of the scaffold significantly ($p<0.0001$) increased to 185.5±1.5 mN (FIG. 16). This demonstrates that cells seeded in the scaffolds add to the mechanical integrity of scaffold by tissue remodelling mechanism.

The calculated break strength for the 3A 74.33±3.78 mN, 119.33±33.12 nN for 3B, 103.34±20.23 mN for 3C and 71.68±4.72 mN for 3D. This demonstrates that after adding another co-polymer the mechanical properties of elastin decrease. It is believed that this is due to the non-fibril arrangement of the polymers (Lake et al. (2012)).

EXAMPLE 7—ANGIOGENESIS

Pathogen-free fertilised eggs were obtained from a commercial supplier and incubated for 3 days at 38° C. with 40-45% humidity. On an, embryonic day (ED), 3 (ED 3) ex ovo glass bowl set-up was constructed to grow the embryonic culture and maintained at 37.5° C. with 3% $CO_2$ and an average humidity in the range of 80-85% (3). At ED 9 elastin scaffold were placed on the developing chorio-allantoic membrane (CAM) to allow infiltration of blood vessels and at ED 12 embryos were euthanised as per home office guideline, and scaffolds were excised and fixed in 4% glutaraldehyde and analysed.

Figure 18:
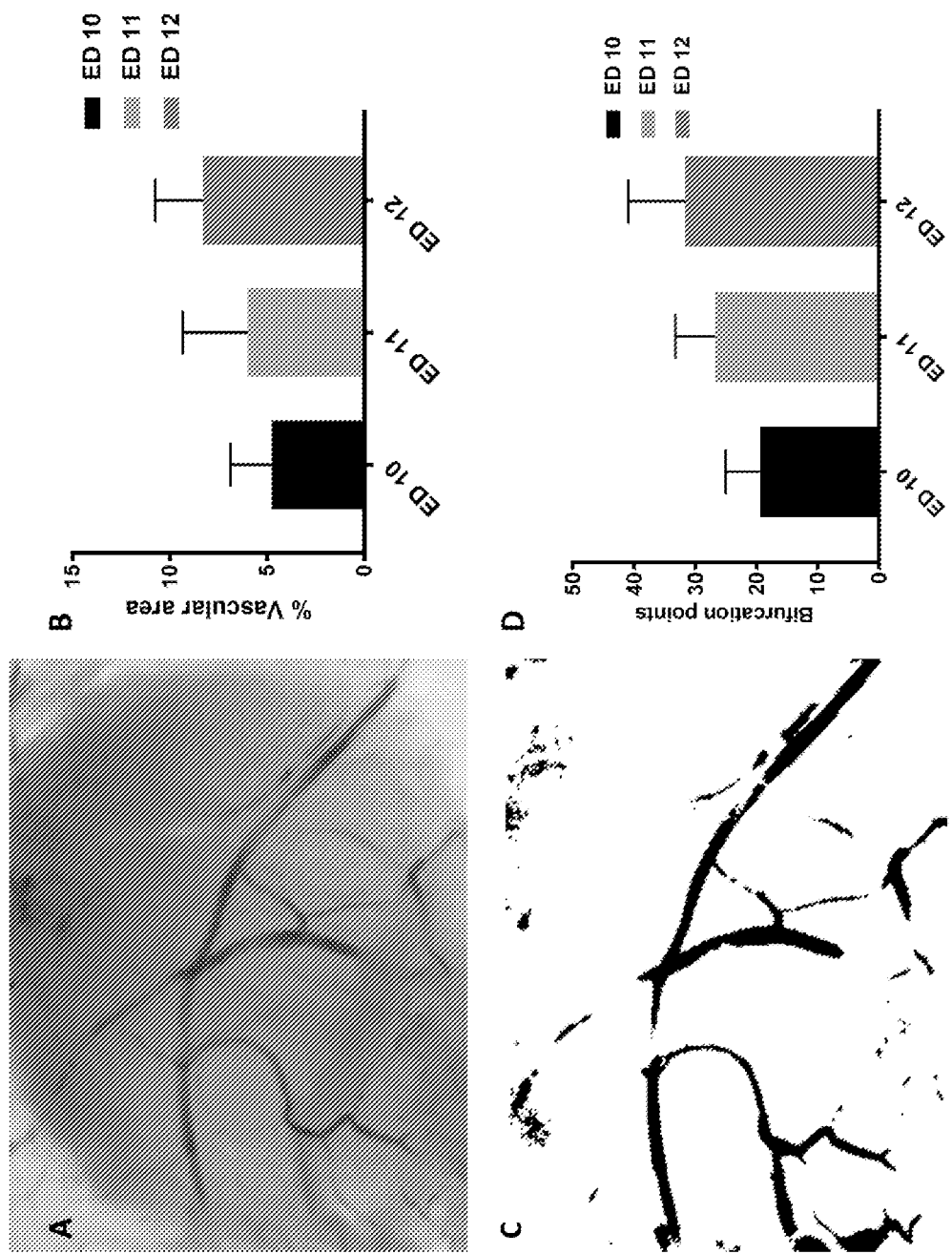
FIG. 18 shows developing chorio-allantoic membrane (CAM) on an elastin scaffold on embryonic day (ED) 12 (A), total vascular area (B), the processed image for CAM analysis (C) and a number of bifurcation points (D)

A total calculated vascular area for ED 10 was 4.78±2.12% and this vascular area increased to 6.01±3.34% at ED 11 although this increment was not statistically significant but developed two large vessels with a number of capillary plexus. This trend continues to follow on ED 12 with the calculated vascular area was 8.34±2.67% (FIG. 18).

Figure 19:
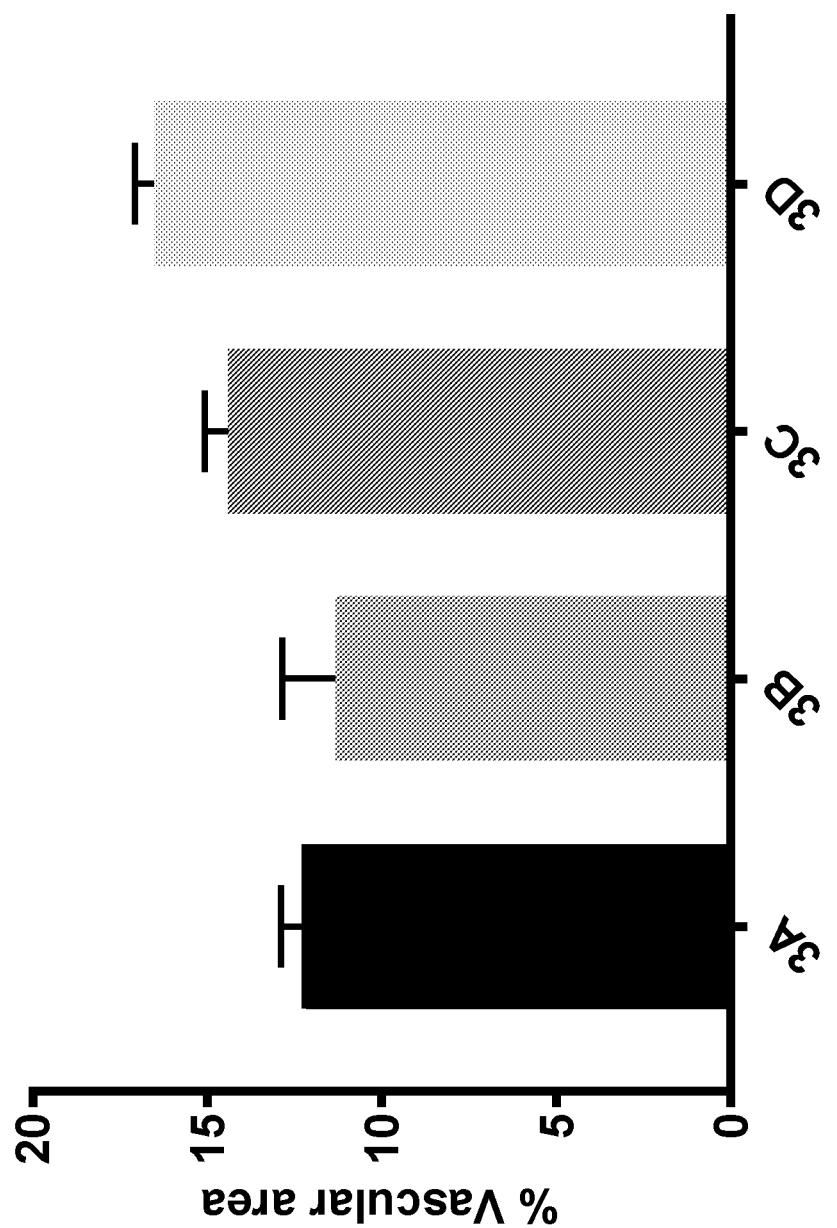
FIG. 19 shows Vascular area (%) for elastin-based composite scaffolds.

When elastin was combined with fibrin and collagen, in different ratios, then there was an increase in the total vascular area % by day 12. The calculated % vascular area was 12.97±0.61% for 3A, 11.33±1.52% for 3B, 14.41±0.67% for 3C and 16.52±0.57 for 3D (FIG. 19).

Therefore, it appears beneficial to use a combination of polymers to enhance angiogenetic properties of elastin. A CAM assay acted as ex vivo bioreactor to understand vascular invasion into the elastin-based scaffolds. In view that scaffolds have pore distribution in the range of 0 μm-120+μm which act as a pro-angiogenetic material for blood vessels infiltration.

EXAMPLE 8—CELLULAR DIFFERENTIATION

To understand human adipose-derived cells (hADSCs) differentiation pathway on the elastin scaffold, a total $5\times10^5$/$mm^3$ hADSC of passage 4 seeded on scaffolds. RNA was isolated by using TRIzol (Invitrogen, Paisley, UK) method on day 1, 7 14 and total RNA yield was quantified by using spectrophotometer (Spectronic Camspec Ltd, Garforth, UK). cDNA synthesis was carried out using Precision nanoscript 2 reverse transcription kit (Primer Design, Southampton, UK) and quantitative PCR was performed with custom designed and synthesised primers (Table 1) (Primer Design, Southampton, UK).

TABLE 1

| Name of gene | Forward and reverse primers | |
|---|---|---|
| | Forward primer | Reverse primer |
| MYOD1 | CGCCTGAGCAAAGTAAATGAG (SEQ ID: 1) | GCCCTCGATATAGCGGATG (SEQ ID: 2) |
| PPARG | GAATAAAGATGGGGTTCTCAT ATCC (SEQ ID: 3) | AACTTCAGCAAACTCAAACTT (SEQ ID: 4) |
| CEBPA | CGGCAACTCTAGTATTTAGGA TAAC (SEQ ID: 5) | CAAATAAAATGACAAGGCAC GATT (SEQ ID: 6) |
| RUNX2 | TTCTCCCCTTTTCCCACTGA (SEQ ID: 7) | CAAACGCAATCACTATCTAT ACCAT (SEQ ID: 8) |
| SOX9 | GGACCAGTACCCGCACTTG (SEQ ID: 9) | AATCCGGGTGGTCCTTCTTG (SEQ ID: 10) |
| OCT4 | CACTAAGGAAGGAATTGGGA ACA (SEQ ID: 11) | GGGATTAAAATCAAGAGCAT CATTG (SEQ ID: 12) |
| REX1 | CGTTTCGTGTCCCTTTCA (SEQ ID: 13) | CCTCTTGTTCATTCTTGTTCGT ATT(SEQ ID: 14) |

Gene expression of and mesenchymal lineage-specific differentiation markers Adipogenic (CEBPA and PPARG), Osteogenic (RUNX2), Myogenic (MYOD1), Chondrogenic (SOX9) and MSC markers (OCT4 and REX1) were studied in hADSCs.

Figure 20:
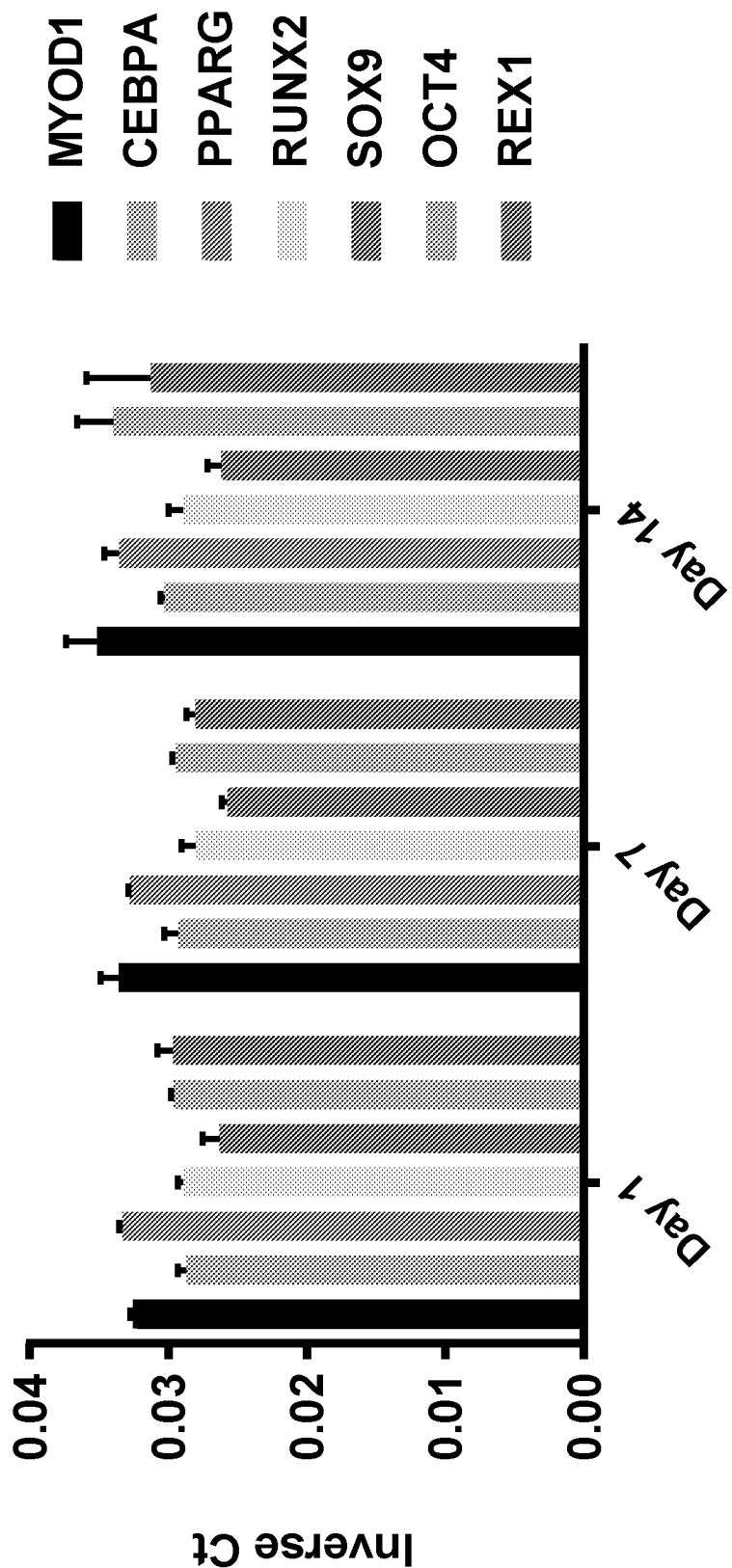
FIG. 20 shows a gene expression profile of an elastin scaffold.
Figure 21:
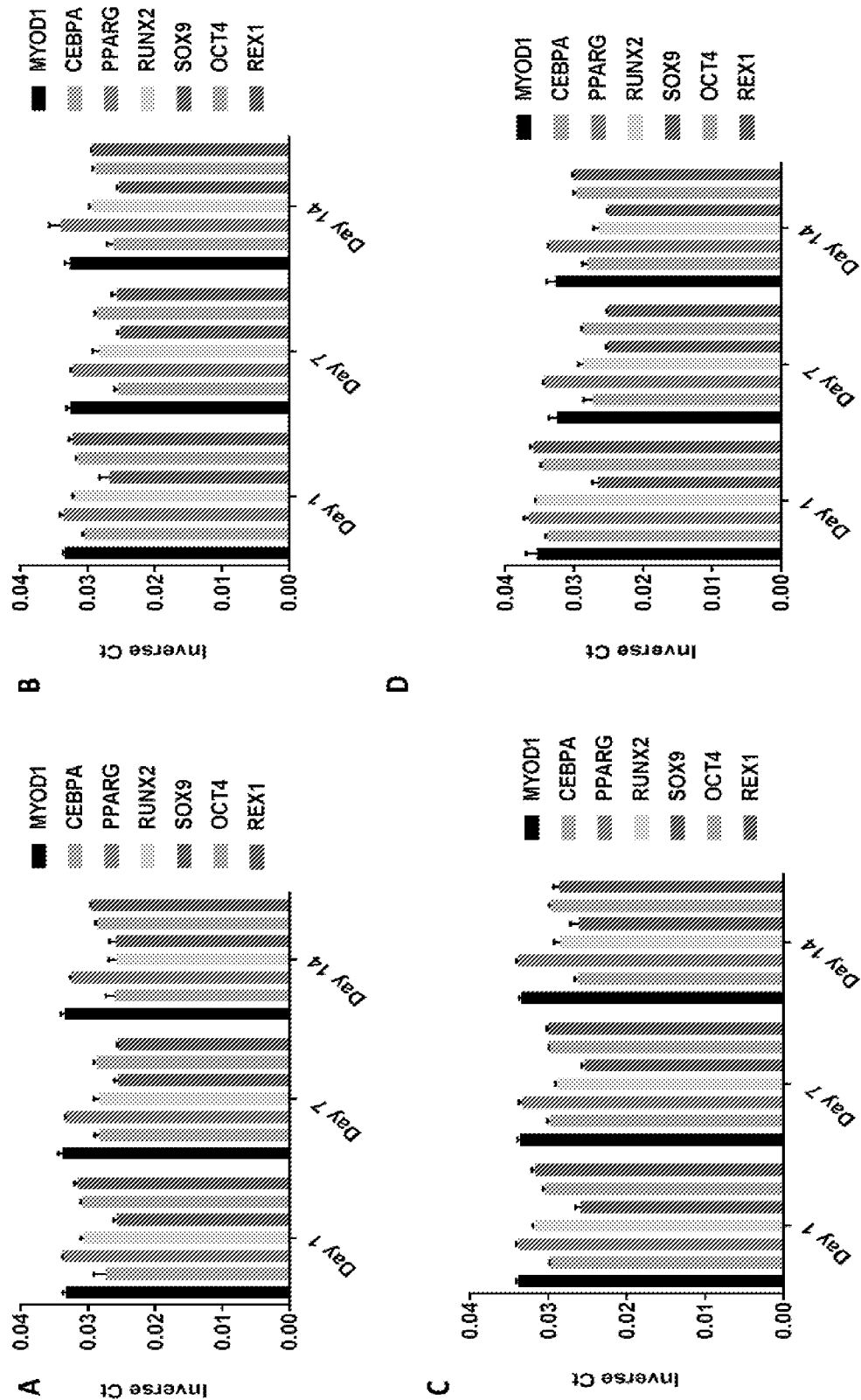
FIG. 21 shows gene expression profiles for elastin-based composite scaffolds.

Differentiation profile of hADSC on the elastin scaffold. OCT4, CEBPA, PPARG and MYOD1 showed an identical trend of significant upregulation by 0.03-0.04 units on day 7 and 14 in comparison to day 1 ($p<0.0001$). However, there was no significant upregulation on day 14 in comparison to day 7. RUNX2 did not show any trend. SOX9 exhibited negligible expression (<0.027) at all three-time points identical to all the other scaffolds reported above, although it showed a significant upregulation on day 14 (0.025, $p<0.05$) in comparison to day 1 (0.027). REX1 exhibited an initial downregulation on day 7 (0.036 to 0.028, $p<0.0001$), followed by a significant upregulation trend on day 14 (0.031, $p<0.0001$) (FIG. 20).

In 3A, Oct-4 shows significant downregulation on day 7 and 14 (0.028, $p<0.0001$) from day 1 (0.031). Rex-1 down-regulated significantly on day 7 (0.026, $p<0.0001$) and 14

(0.029, p<0.0001) in comparison to day 1 (0.031). However, expression on day 14 was significantly higher than day 7 (p<0.0001), whereas MyoD-1 was constant at 0.032. CEBP showed a marginal upregulation on day 7 (p<0.05) and significantly downregulated to 0.025 on day 14 (p<0.0001). In 3B, Oct-4, RUX-2 and CEBP showed significant downregulation on day 7 and 14 (p<0.0001) in comparison and there was no significant difference between expression on day 7 and 14. In 3C, Oct-4 showed a steady and significant downregulation from 0.030 on day to 0.029 on day 14 (p<0.001). Rex-1 and RUNX-2 downregulated significantly (p<0.0001) from 0.032 on day 1 to 0.030 and 0.029 respectively on day 7. In 3D, Oct-4, CEBP, PPAR-gamma and MyoD-1 showed identical trend of significant downregulation by 0.04-0.06 units on day 7 and 14 in comparison to day 1 (p<0.0001)

EXAMPLE 9—BINARY ELASTIN-BASED SCAFFOLDS

Elastin/Collagen—1:1 ratio
Elastin/Fibrin—1:1 ratio
The elastin, collagen and fibrin were prepared as shown in Example 2.

Swelling ratio

Figure 22:
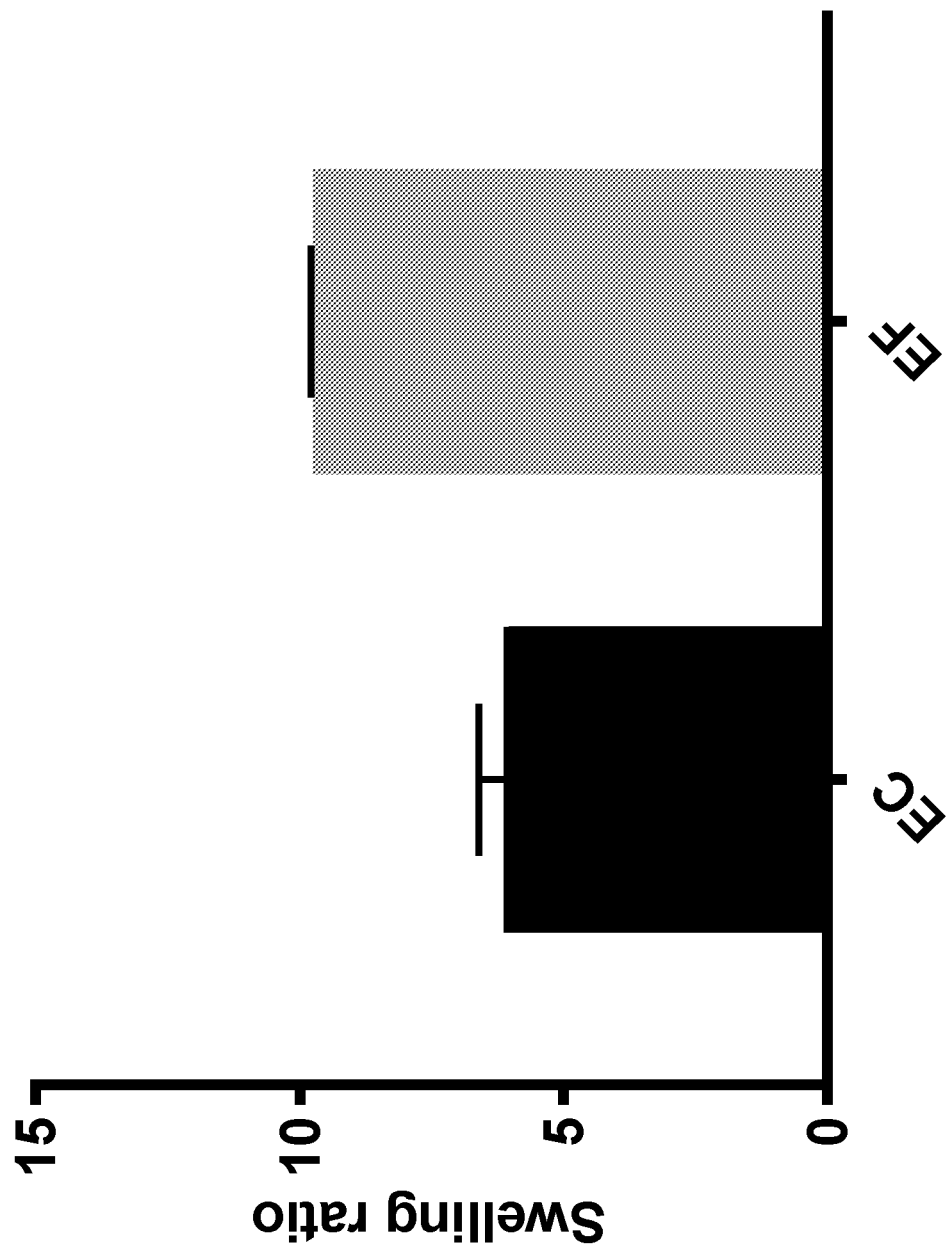
FIG. 22 shows the difference in swelling ratio between Elastin/Collagen and Elastin/Fibrin scaffolds.

FIG. 22 shows the difference in swelling ratio between Elastin/Collagen and Elastin/Fibrin scaffolds. Swelling ratio is an indication of the interaction between a solvent and a polymer. It shows exchange of the affinity and enthalpy between two phases. The higher the crosslinking density inside a polymer then the lower the swelling property, and vice-versa. The swelling ratio (SR) of the elastin and its composites was measured from dry mass and wet mass with the following equation $$SR = \frac{M_w - M_d}{M_w} \quad (1)$$

where $M_d$ is the dry weight of the scaffold and $M_w$ is the wet weight of the scaffold. A wet mass of the scaffold was measured by immersing into 2 ml of distilled water. Dry and wet mass measured with the digital scale (XS205 Mettler Toledo®) and the SR was calculated using equation (1)

Degradation

Figure 23:
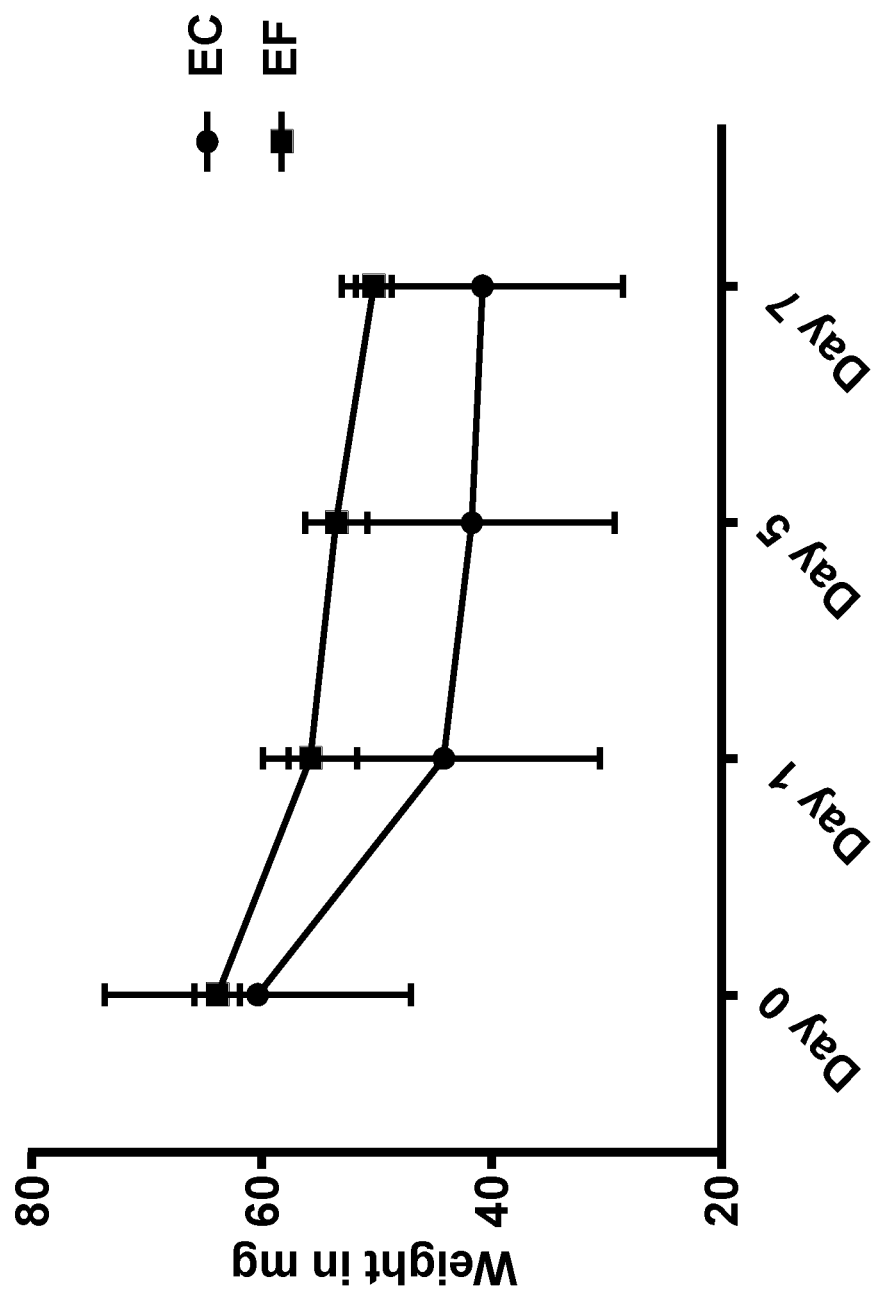
FIG. 23 shows the difference in degradation profiles between Elastin/Collagen and Elastin/Fibrin scaffolds.

FIG. 23 shows the difference in degradation profiles between Elastin/Collagen and Elastin/Fibrin scaffolds. The experimental protocol was the same as described in Example 4.

Microstructure

Figure 24:
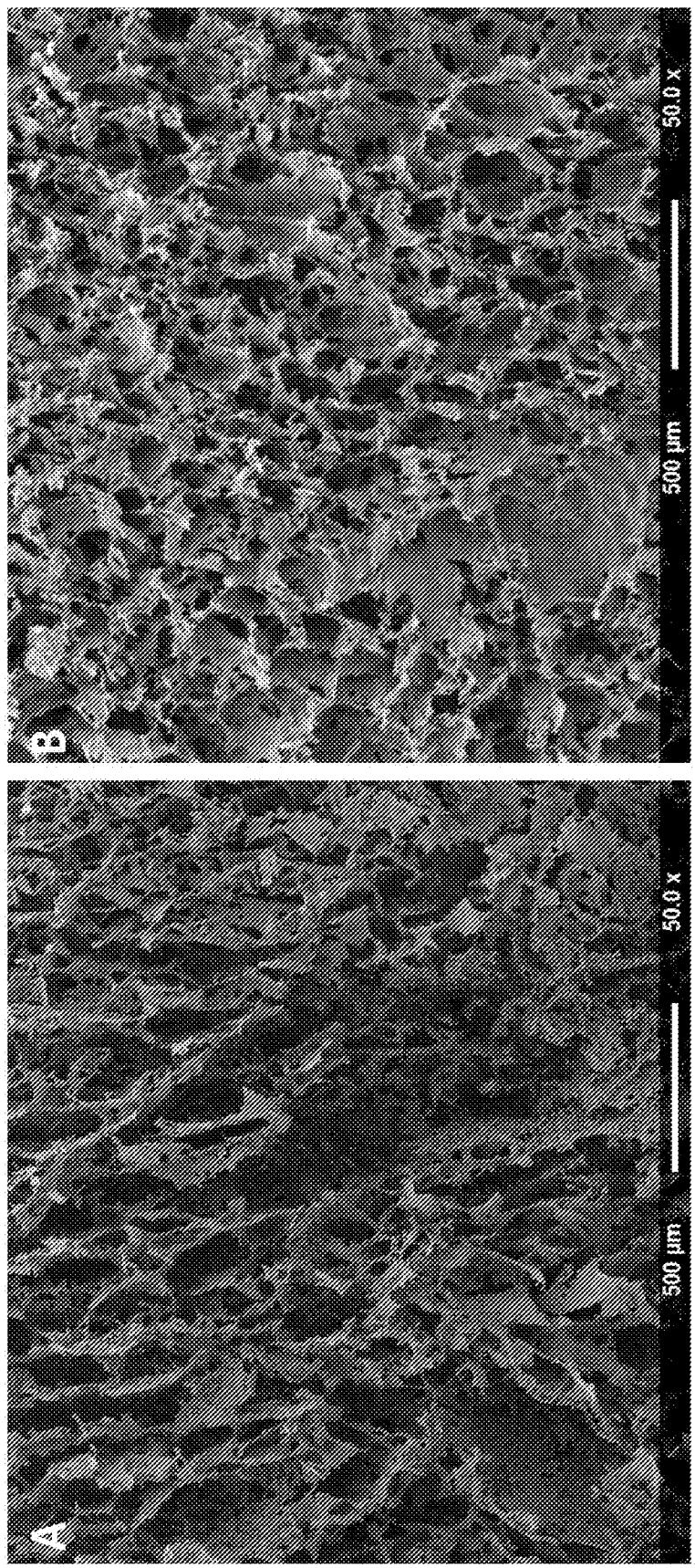
FIG. 24 shows the microstructure of Elastin/Collagen and Elastin/Fibrin scaffolds using SEM.

FIG. 24 shows the microstructure of Elastin/Collagen (A) and Elastin/Fibrin (B) scaffolds using SEM.

Pore size distribution

Figure 25:
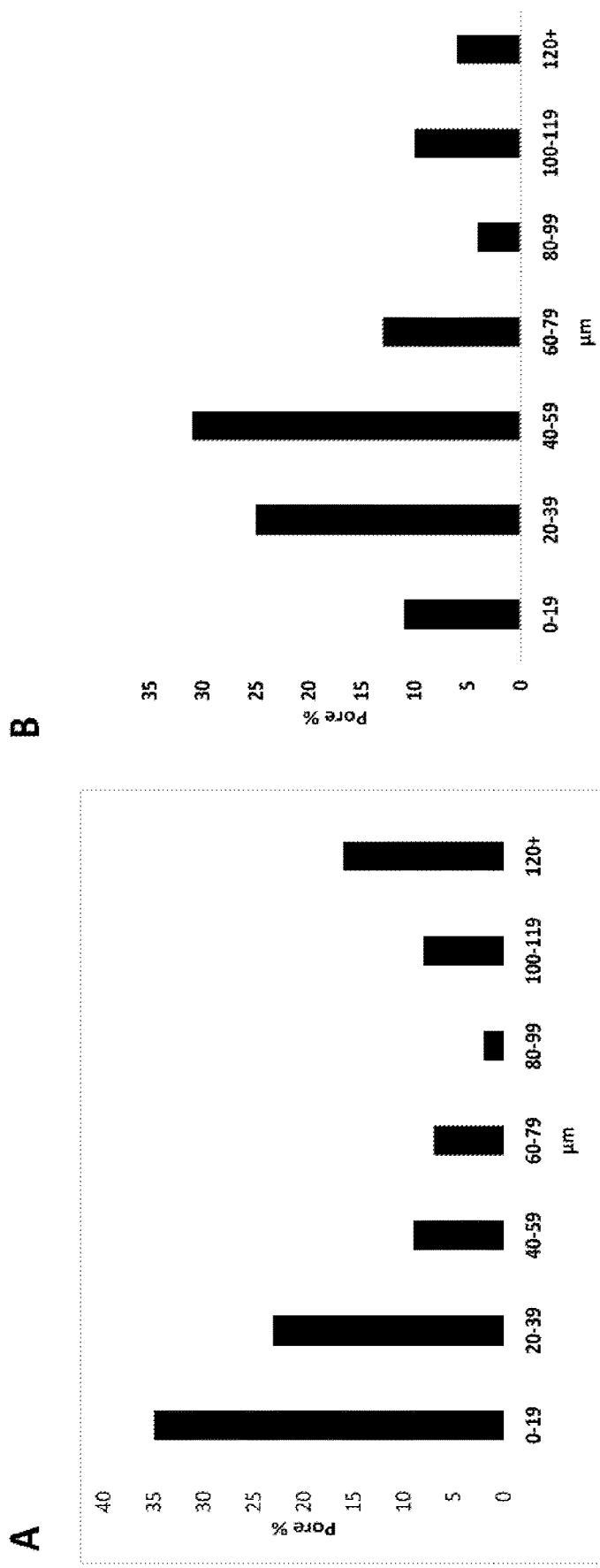
FIG. 25 shows the pore size of distribution of Elastin/Collagen and Elastin/Fibrin scaffolds.

FIG. 25 shows the pore size of distribution of Elastin/Collagen and Elastin/Fibrin scaffolds.

Biological activity

Figure 26:
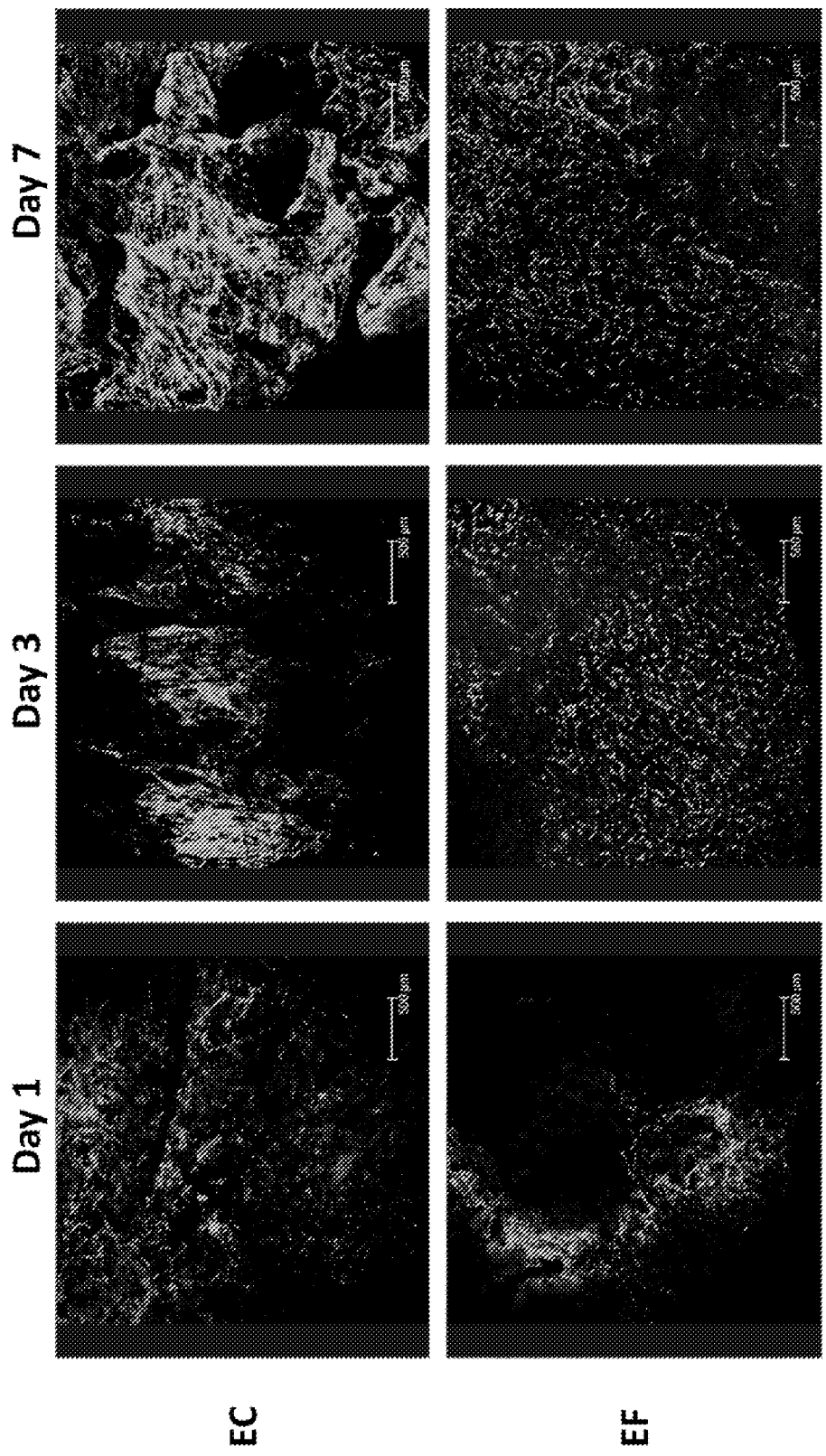
FIG. 26 shows the results of a live/dead assay for Elastin/Collagen and Elastin/Fibrin scaffolds.

FIG. 26 shows the results of a live/dead assay for Elastin/Collagen and Elastin/Fibrin scaffolds. The experimental protocol was the same as described in Example 1.

Angiogenesis

Figure 27:
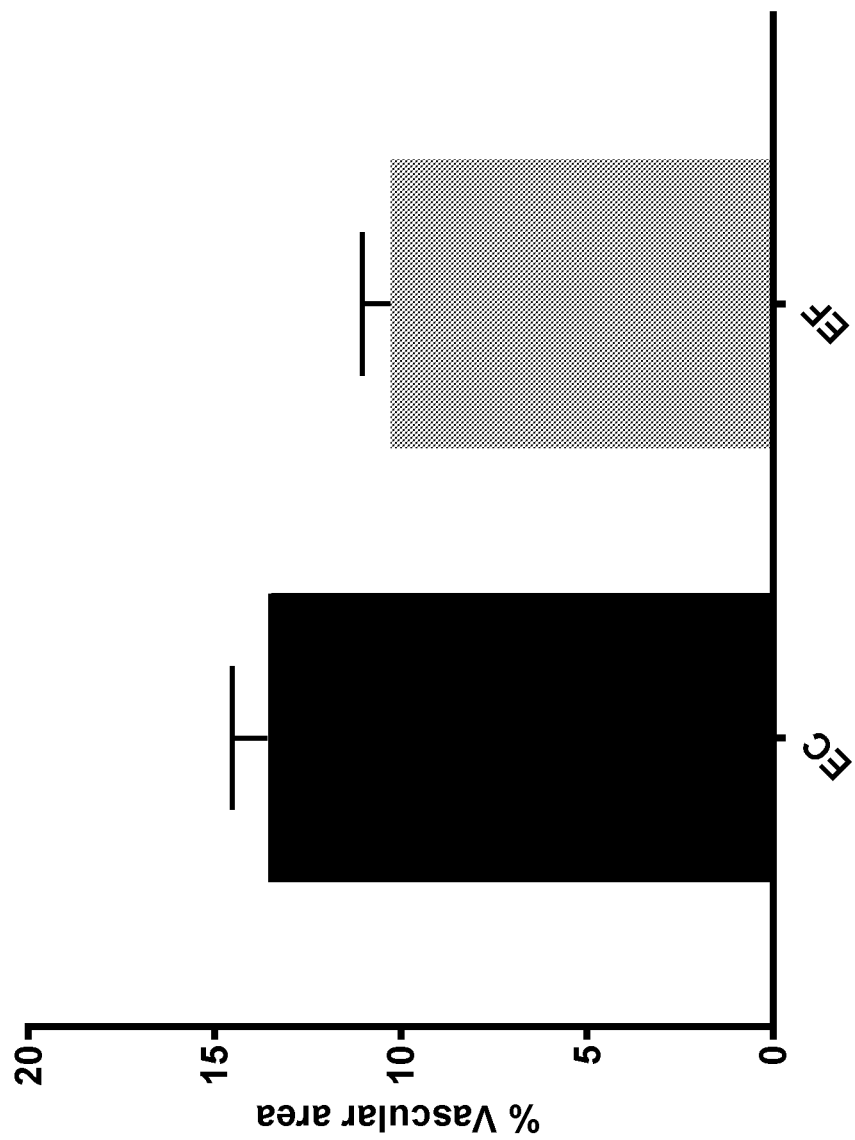
FIG. 27 shows the vascular area for Elastin/Collagen and Elastin/Fibrin scaffolds at day 12.

FIG. 27 shows the vascular area for Elastin/Collagen and Elastin/Fibrin scaffolds at day 12. The experimental protocol was the same as described in Example 7.

REFERENCES

ADAIR, G. S., DAVIS, H. F. & PARTRIDGE, S. M. 1951. A Soluble Protein derived from Elastin. *Nature*, 167, 605-605.

ANNABI, N., MITHIEUX, S. M., BOUGHTON, E. A., RUYS, A. J., WEISS, A. S. & DEHGHANI, F. 2009. Synthesis of highly porous crosslinked elastin hydrogels and their interaction with fibroblasts in vitro. *Biomaterials*, 30, 4550-4557.

BANGA, I. 1966. Structure and function of elastin and collagen.

BUTTAFOCO, L., KOLKMAN, N., ENGBERS-BUIJTENHUIJS, P., POOT, A., DIJKSTRA, P., VERMES, I. & FEIJEN, J. 2006. Electrospinning of collagen and elastin for tissue engineering applications. *Biomaterials*, 27, 724-734.

DAAMEN, W. F., VEERKAMP, J. H., VAN HEST, J. C. M. & VAN KUPPEVELT, T. H. 2007. Elastin as a biomaterial for tissue engineering. *Biomaterials*, 28, 4378-4398.

GRAY, W. R. 1973. Molecular model for elastin structure and function. *Nature*, 246, 461-466.

HUANG, W., ROLLETT, A. & KAPLAN, D. L. 2015. Silk-elastin-like protein biomaterials for the controlled delivery of therapeutics. *Expert Opin Drug Deliv,* 12, 779-91.

LEACH, J. B., WOLINSKY, J. B., STONE, P. J. & WONG, J. Y. 2005. Crosslinked alpha-elastin biomaterials: towards a processable elastin mimetic scaffold. *Acta Biomater,* 1, 155-64.

NIVISON-SMITH & WEISS 2011 Regenerative Medicine and Tissue Engineering—Cells and Biomaterials Chapter 15—Elastin Based Constructs ISBN978-953-307-663-8 DOI:10.5772/837

MAJD, H., QUINN, T. M., WIPFF, P. J. & HINZ, B. 2011. Dynamic expansion culture for mesenchymal stem cells. *Methods Mol Biol,* 698, 175-88.

RYAN, A. J. & O'BRIEN, F. J. 2015. Insoluble elastin reduces collagen scaffold stiffness, improves viscoelastic properties, and induces a contractile phenotype in smooth muscle cells. *Biomaterials,* 73, 296-307.

SKOPINSKA-WISNIEWSKA, J., KUDERKO, J., BAJEK, A., MAJ, M., SIONKOWSKA, A. & ZIEGLER-BOROWSKA, M. 2016. Collagen/elastin hydrogels cross-linked by squaric acid. *Mater Sci Eng C Mater Biol Appl,* 60, 100-8.

STOKLASOVA, A., RANDOVA, Z., ROCKOVA, V. & LEDVINA, M. 1992. Soluble elastins, their preparation and characterization. *Sb Ved Pr Lek Fak Karlovy Univerzity Hradci Kralove,* 35, 217-23.

ZHANG, D. & KILIAN, K. A. 2013. The effect of mesenchymal stem cell shape on the maintenance of multipotency. *Biomaterials,* 34, 3962-9.

GHASEMI-MOBARAKEH, LALEH ET AL. 2015 "Structural Properties of Scaffolds: Crucial Parameters towards Stem Cells Differentiation." World Journal of Stem Cells 7.4 (2015): 728-744. PMC. Web.

FU W, LIU Z, FENG B, HU R, HE X, WANG H 2014 Electrospun gelatin/PCL and collagen/PLCL scaffolds for vascular tissue engineering. *Int J Nanomedicine.;* 9:2335-44.

LAKE S P, HADI M F, LAI V K, BAROCAS V H. 2012. Mechanics of a fiber network within a non-fibrillar matrix: model and comparison with collagen agarose co-gels. *Annals of biomedical engineering.* 40(10):2111-21.

AUERBACH R, KUBAI L, KNIGHTON D, FOLKMAN J. 1974. A simple procedure for the long-term cultivation of chicken embryos. *Dev Biol.;* 41(2):391-4.

The invention claimed is:

1. A method for forming a tissue scaffold, comprising cross-linking a composition, the composition comprising elastin, collagen, and fibrin; wherein the elastin comprises solubilised elastin and insoluble elastin.

2. The method of claim 1, further comprises a step of solubilising elastin.

3. The method of claim 1, wherein the elastin is solubilised by contacting with oxalic acid.

4. The method of claim 2, wherein the step of solubilising the elastin is carried out at a temperature less than or equal to 50° C.

5. The method of claim 1, wherein the collagen is in the form of a collagen hydrogel.

6. The method of claim 1, wherein the fibrin is in the form of a fibrin gel.

7. The method of claim 1, wherein the cross-linking is chemical cross-linking.

8. The method of claim 7, wherein the chemical cross-linking comprises contacting the composition with an aldehyde cross-linking agent.

9. The method of claim 8, wherein the aldehyde cross-linking agent is glutaraldehyde.

10. The method of claim 1, wherein the cross-linking takes place in the presence of $CO_2$.

11. The method according to claim 10, wherein the cross-linking takes place in the presence of 2 to 10% $CO_2$.

12. The method of claim 1, further comprising lyophilising the composition following the cross-linking.

13. The method of claim 1, further comprising washing to remove agents involved in solubilising and/or cross-linking.

14. The method of claim 13 further comprising lyophilisation prior to the washing.

15. The method of claim 13, wherein the washing comprises washing with a reducing agent.

16. The method of claim 15, wherein the reducing agent is selected from the group consisting of sodium borohydride and agents with similar carbonyl group reactivity.

17. The method of claim 1, further comprising sterilising the scaffold.

18. The method according to claim 17, wherein the sterilising of the scaffold comprising contacting the scaffold with ethanol.

\* \* \* \* \*